US010967556B2

(12) United States Patent
Wang et al.

(10) Patent No.: US 10,967,556 B2
(45) Date of Patent: Apr. 6, 2021

(54) UNIFORM EXPANSION OF THIN-WALLED SCAFFOLDS

(71) Applicant: Abbott Cardiovascular Systems Inc., Santa Clara, CA (US)

(72) Inventors: Karen J. Wang, Sunnyvale, CA (US); Boyd V. Knott, Menifee, CA (US); Edward P. Garcia, Dublin, CA (US)

(73) Assignee: ABBOTT CARDIOVASCULAR SYSTEMS INC., Santa Clara, CA (US)

( * ) Notice: Subject to any disclaimer, the term of this patent is extended or adjusted under 35 U.S.C. 154(b) by 249 days.

(21) Appl. No.: 16/005,524

(22) Filed: Jun. 11, 2018

(65) Prior Publication Data

US 2019/0375146 A1 Dec. 12, 2019

(51) Int. Cl.
| B29C 53/08 | (2006.01) |
| A61F 2/958 | (2013.01) |
| B29L 31/00 | (2006.01) |

(52) U.S. Cl.
CPC ............ *B29C 53/086* (2013.01); *A61F 2/958* (2013.01); *A61F 2002/9583* (2013.01); *A61F 2230/006* (2013.01); *A61F 2230/0013* (2013.01); *A61F 2230/0056* (2013.01); *A61F 2240/001* (2013.01); *A61F 2250/0096* (2013.01); *B29L 2031/7534* (2013.01)

(58) Field of Classification Search
None
See application file for complete search history.

(56) References Cited

U.S. PATENT DOCUMENTS

| 5,261,263 A | 11/1993 | Whitesell |
| 5,556,383 A | 9/1996 | Wang et al. |
| 5,672,169 A | 9/1997 | Verbeek |
| 5,836,965 A | 11/1998 | Jendersee et al. |
| 5,913,871 A | 6/1999 | Werneth et al. |
| 5,976,181 A | 11/1999 | Whelan et al. |
| 5,992,000 A | 11/1999 | Humphrey et al. |
| 6,018,857 A | 2/2000 | Duffy et al. |
| 6,063,092 A | 5/2000 | Shin |

(Continued)

FOREIGN PATENT DOCUMENTS

| CN | 1260213 | 7/2000 |
| CN | 101015440 | 8/2007 |

(Continued)

OTHER PUBLICATIONS

Invitation to Pay Additional Fees, and, Where Applicable, Protest Fee, in International Patent Application No. PCT/US2019/035564, 18 pages.

(Continued)

*Primary Examiner* — Monica A Huson
(74) *Attorney, Agent, or Firm* — Squire Patton Boggs (US) LLP

(57) ABSTRACT

A medical device includes a balloon expanded scaffold (or stent) crimped to a catheter having a balloon. The scaffold is crimped to the balloon by a process that includes using protective polymer sheaths or sheets during crimping, and resetting the sheaths or sheets during the crimping to avoid or minimize interference between the polymer material and scaffold struts as the scaffold is reduced in size. Balloon pressure is adjusted when the polymer material is reset.

19 Claims, 11 Drawing Sheets

(56) References Cited

U.S. PATENT DOCUMENTS

| | | |
|---|---|---|
| 6,092,526 A | 7/2000 | LaFontaine et al. |
| 6,179,867 B1 | 1/2001 | Cox |
| 6,305,436 B1 | 10/2001 | Andersen et al. |
| 6,312,459 B1 | 11/2001 | Huang et al. |
| 6,360,577 B2 | 3/2002 | Austin |
| 6,488,688 B2 | 12/2002 | Lim et al. |
| 6,629,350 B2 | 10/2003 | Motsenbocker |
| 6,666,880 B1 | 12/2003 | Chiu et al. |
| 6,745,445 B2 | 6/2004 | Spilka |
| 6,783,542 B2 | 8/2004 | Eidenschink |
| 6,805,703 B2 | 10/2004 | McMorrow |
| 6,863,683 B2 | 3/2005 | Schwager et al. |
| 6,931,899 B2 | 8/2005 | Goff et al. |
| 7,010,850 B2 | 3/2006 | Hijlkema et al. |
| 7,156,869 B1 | 1/2007 | Pacetti |
| 7,316,148 B2 | 1/2008 | Asmus et al. |
| 7,389,670 B1 | 6/2008 | Kokish et al. |
| 7,563,400 B2 | 7/2009 | Wilson et al. |
| 7,648,727 B2 | 1/2010 | Hossainy et al. |
| 7,761,968 B2 | 7/2010 | Huang et al. |
| 7,762,804 B1 | 7/2010 | Stupecky |
| 7,763,198 B2 | 7/2010 | Knott et al. |
| 7,886,419 B2 | 2/2011 | Huang et al. |
| 7,945,409 B2 | 5/2011 | Furst et al. |
| 7,947,207 B2 | 5/2011 | McNiven et al. |
| 7,951,185 B1 | 5/2011 | Abbate et al. |
| 7,971,333 B2 | 7/2011 | Gale et al. |
| 8,002,817 B2 | 8/2011 | Limon |
| 8,046,897 B2 | 11/2011 | Wang et al. |
| 8,123,793 B2 | 2/2012 | Roach et al. |
| 8,225,474 B2 | 7/2012 | Arcand et al. |
| 8,261,423 B2 | 9/2012 | Jow et al. |
| 8,323,760 B2 | 12/2012 | Zheng et al. |
| 8,425,587 B2 | 4/2013 | Trollsas et al. |
| 8,539,663 B2 | 9/2013 | Wang et al. |
| 8,568,471 B2 | 10/2013 | Trollsas et al. |
| 8,595,913 B2 | 12/2013 | Knott et al. |
| 8,726,483 B2 | 5/2014 | Stankus et al. |
| 8,752,261 B2 | 6/2014 | Van Sciver |
| 8,752,265 B2 | 6/2014 | Wang |
| 8,844,113 B2 | 9/2014 | Wang |
| 8,961,848 B2 | 2/2015 | Roberts et al. |
| RE45,744 E | 10/2015 | Gale et al. |
| 9,155,870 B2 | 10/2015 | Wang |
| 9,199,408 B2 | 12/2015 | Wang et al. |
| 9,283,100 B2 | 3/2016 | Wang et al. |
| 9,308,106 B2 | 4/2016 | Knott et al. |
| 9,642,729 B2 | 5/2017 | Wang et al. |
| 9,681,971 B2 | 6/2017 | Wang |
| 9,724,219 B2 | 8/2017 | Wang |
| 9,895,241 B2 | 2/2018 | Wang |
| 9,931,787 B2 | 4/2018 | Harrington et al. |
| 9,999,527 B2 | 6/2018 | Pacetti et al. |
| 2002/0035774 A1 | 3/2002 | Austin |
| 2002/0143382 A1 | 10/2002 | Hijlkema et al. |
| 2003/0070469 A1 | 4/2003 | Kokish |
| 2004/0078953 A1 | 4/2004 | Spilka |
| 2004/0096538 A1 | 5/2004 | Goff et al. |
| 2004/0106973 A1 | 6/2004 | Johnson |
| 2004/0138731 A1 | 7/2004 | Johnson |
| 2004/0181236 A1 | 9/2004 | Eidenschink et al. |
| 2004/0260379 A1 | 12/2004 | Jagger et al. |
| 2005/0119720 A1 | 6/2005 | Gale et al. |
| 2005/0143752 A1 | 6/2005 | Schwager et al. |
| 2005/0159802 A1 | 7/2005 | Furst et al. |
| 2005/0183259 A1 | 8/2005 | Eidenschink et al. |
| 2005/0188525 A1 | 9/2005 | Weber et al. |
| 2005/0229670 A1 | 10/2005 | Perreault |
| 2005/0244533 A1 | 11/2005 | Motsenbocker et al. |
| 2005/0283225 A1 | 12/2005 | Klisch |
| 2006/0004469 A1 | 1/2006 | Sokel |
| 2006/0047336 A1 | 3/2006 | Gale et al. |
| 2006/0100694 A1 | 5/2006 | Globerman |
| 2006/0116748 A1 | 6/2006 | Kaplan et al. |
| 2006/0123874 A1 | 6/2006 | Motsenbocker |
| 2006/0196073 A1 | 9/2006 | Parker |
| 2007/0006441 A1 | 1/2007 | McNiven et al. |
| 2007/0023974 A1 | 2/2007 | Wu |
| 2007/0204455 A1 | 9/2007 | Knott et al. |
| 2007/0259099 A1 | 11/2007 | Van Sciver |
| 2007/0271763 A1 | 11/2007 | Huang et al. |
| 2007/0282433 A1 | 12/2007 | Limon et al. |
| 2007/0289117 A1 | 12/2007 | Huang et al. |
| 2007/0293938 A1 | 12/2007 | Gale et al. |
| 2008/0016668 A1 | 1/2008 | Huang et al. |
| 2008/0033523 A1 | 2/2008 | Gale et al. |
| 2008/0033524 A1 | 2/2008 | Gale |
| 2008/0033526 A1 | 2/2008 | Atladottir et al. |
| 2008/0072653 A1 | 3/2008 | Gillick et al. |
| 2008/0127707 A1 | 6/2008 | Kokish et al. |
| 2008/0147164 A1 | 6/2008 | Gale et al. |
| 2008/0208327 A1 | 8/2008 | Rowe |
| 2008/0275537 A1 | 11/2008 | Limon |
| 2009/0001633 A1 | 1/2009 | Limon et al. |
| 2009/0088829 A1 | 4/2009 | Wang et al. |
| 2009/0105800 A1 | 4/2009 | Sabaria |
| 2009/0133817 A1 | 5/2009 | Sabaria |
| 2009/0228094 A1 | 9/2009 | Yan et al. |
| 2009/0282669 A1 | 11/2009 | von Oepen et al. |
| 2009/0287289 A1 | 11/2009 | Sagedahl et al. |
| 2009/0299452 A1 | 12/2009 | Eidenschink et al. |
| 2010/0004735 A1 | 1/2010 | Yang et al. |
| 2010/0025894 A1 | 2/2010 | Kleiner et al. |
| 2010/0063571 A1 | 3/2010 | Roach et al. |
| 2010/0087782 A1 | 4/2010 | Ghaffari et al. |
| 2010/0115755 A1 | 5/2010 | Pacetti |
| 2010/0286758 A1 | 11/2010 | Berglund |
| 2010/0323091 A1 | 12/2010 | Castro et al. |
| 2011/0152905 A1 | 6/2011 | Eaton |
| 2011/0190872 A1 | 8/2011 | Anukhin et al. |
| 2011/0270383 A1 | 11/2011 | Jow et al. |
| 2011/0271513 A1 | 11/2011 | Wang |
| 2011/0307046 A1 | 12/2011 | Bourang et al. |
| 2012/0010693 A1 | 1/2012 | Van Sciver |
| 2012/0017416 A1 | 1/2012 | Wang et al. |
| 2012/0042501 A1 | 2/2012 | Wang et al. |
| 2012/0079706 A1 | 4/2012 | Knott et al. |
| 2012/0285609 A1 | 11/2012 | Wang |
| 2012/0316635 A1 | 12/2012 | Jow et al. |
| 2013/0255853 A1 | 10/2013 | Wang et al. |
| 2014/0013575 A1 | 1/2014 | Wang et al. |
| 2014/0033506 A1 | 2/2014 | Jow et al. |
| 2014/0096357 A1 | 4/2014 | Wang |
| 2014/0189994 A1 | 7/2014 | Van Sciver |
| 2014/0230225 A1 | 8/2014 | Van Sciver |
| 2014/0330363 A1 | 11/2014 | Anukhin et al. |
| 2014/0336747 A1 | 11/2014 | Rapoza et al. |
| 2015/0059960 A1 | 3/2015 | Roberts et al. |
| 2015/0224707 A1* | 8/2015 | Wang .................... A61F 2/958 156/84 |
| 2015/0257907 A1 | 9/2015 | Vial et al. |
| 2016/0081824 A1 | 3/2016 | Harrington et al. |
| 2017/0172768 A1 | 6/2017 | Ta et al. |
| 2017/0348124 A1 | 12/2017 | Wang |
| 2018/0116830 A1 | 5/2018 | Wang |
| 2018/0228630 A1 | 8/2018 | Wang et al. |
| 2019/0133798 A1 | 5/2019 | Gong et al. |

FOREIGN PATENT DOCUMENTS

| | | |
|---|---|---|
| EP | 0 787 020 | 8/1997 |
| EP | 1 000 591 | 5/2000 |
| EP | 1 226 798 | 7/2002 |
| EP | 1 295 570 | 3/2003 |
| EP | 1 818 073 | 8/2007 |
| EP | 2 029 052 | 3/2009 |
| JP | 2005-535459 | 11/2005 |
| JP | 2008-538940 | 11/2008 |
| JP | 2009-540928 | 11/2009 |
| JP | 2009-542263 | 12/2009 |
| JP | 4468333 | 5/2010 |
| JP | 2010-525903 | 7/2010 |
| JP | 2010-540091 | 12/2010 |
| WO | WO 99/55406 | 11/1999 |

(56) References Cited

FOREIGN PATENT DOCUMENTS

| WO | WO 00/36994 | 6/2000 |
|---|---|---|
| WO | WO 01/35861 | 5/2001 |
| WO | WO 02/074192 | 9/2002 |
| WO | WO 02/102283 | 12/2002 |
| WO | WO 2004/016369 | 2/2004 |
| WO | WO 2005/053937 | 6/2005 |
| WO | WO 2006/110861 | 10/2006 |
| WO | WO 2006/117016 | 11/2006 |
| WO | WO 2007/116305 | 10/2007 |
| WO | WO 2007/146354 | 12/2007 |
| WO | WO 2007/146543 | 12/2007 |
| WO | WO 2007/149464 | 12/2007 |
| WO | WO 2008/011028 | 1/2008 |
| WO | WO 2008/033621 | 3/2008 |
| WO | WO 2008/137821 | 11/2008 |
| WO | WO 2009/045764 | 4/2009 |
| WO | WO 2010/036982 | 4/2010 |
| WO | WO 2010/151497 | 12/2010 |
| WO | WO 2011/136929 | 11/2011 |
| WO | WO 2012/006451 | 1/2012 |
| WO | WO 2012/027172 | 3/2012 |
| WO | WO 2012/044454 | 4/2012 |
| WO | WO 2012/145326 | 10/2012 |
| WO | WO 2013/039637 | 3/2013 |

OTHER PUBLICATIONS

International Search Report and Written Opinion, in International Patent Application No. PCT/US2019/035564, 23 pages.
U.S. Appl. No. 11/330,927, filed Jan. 11, 2006, Wu et al.
U.S. Appl. No. 11/938,127, filed Nov. 9, 2007, Wang.
Angioplasty Summit Abstracts/Oral, Am J Cardiol. Apr. 23-26, 2013, p. 23B.
Bosiers et al., "Coronary and endovascular applications of the AbsorbTM bioresorbable vascular scaffold", Interv Cardiol. 2012; 4(6): 621-631.
Miller, R., "Abbott's Bioresorbable Stent Shows Durable Results in ABSORB Trial", The Gray Sheet, Mar. 25, 2013, pp. 17-18.
Zhang et al., "Heparin-and basic fibroblast growth factor—incorporated degradable stent: comparison with traditional transmyocardial revascularization", J Cardiovasc Surg. 2011; 52: 261-270.

* cited by examiner

UNIFORM EXPANSION OF THIN-WALLED SCAFFOLDS

BACKGROUND OF THE INVENTION

Field of the Invention

The present invention relates to medical devices; more particularly, this invention relates to processes for uniformly crimping and deploying a medical device, such as a polymeric scaffold, to and from, respectively, a delivery balloon.

Description of the State of the Art

Radially expandable endoprostheses are artificial devices adapted to be implanted in an anatomical lumen. An "anatomical lumen" refers to a cavity, or duct, of a tubular organ such as a blood vessel, urinary tract, and bile duct. Stents are examples of endoprostheses that are generally cylindrical in shape and function to hold open and sometimes expand a segment of an anatomical lumen. Stents are often used in the treatment of atherosclerotic stenosis in blood vessels. "Stenosis" refers to a narrowing or constriction of the diameter of a bodily passage or orifice. In such treatments, stents reinforce the walls of the blood vessel and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

The treatment of a diseased site or lesion with a stent involves both delivery and deployment of the stent. "Delivery" refers to introducing and transporting the stent through an anatomical lumen to a desired treatment site, such as a lesion. "Deployment" corresponds to expansion of the stent within the lumen at the treatment region. Delivery and deployment of a stent are accomplished by positioning the stent about one end of a catheter, inserting the end of the catheter through the skin into the anatomical lumen, advancing the catheter in the anatomical lumen to a desired treatment location, expanding the stent at the treatment location, and removing the catheter from the lumen.

The stent must be able to satisfy a number of basic, functional requirements. The stent (or scaffold) must be capable of sustaining radial compressive forces as it supports walls of a vessel. Therefore, a stent must possess adequate radial strength. After deployment, the stent must adequately maintain its size and shape throughout its service life despite the various forces that may come to bear on it. In particular, the stent must adequately maintain a vessel at a prescribed diameter for a desired treatment time despite these forces. The treatment time may correspond to the time required for the vessel walls to remodel, after which the stent is no longer needed.

Scaffolds may be made from a biodegradable, bioabsorbable, bioresorbable, or bioerodable polymer. The terms biodegradable, bioabsorbable, bioresorbable, biosoluble or bioerodable refer to the property of a material or stent to degrade, absorb, resorb, or erode away from an implant site. Scaffolds may also be constructed of bioerodible metals and alloys. The scaffold, as opposed to a durable metal stent, is intended to remain in the body for only a limited period of time. In many treatment applications, the presence of a stent in a body may be necessary for a limited period of time until its intended function of, for example, maintaining vascular patency and/or drug delivery is accomplished. Moreover, it has been shown that biodegradable scaffolds allow for improved healing of the anatomical lumen as compared to metal stents, which may lead to a reduced incidence of late stage thrombosis. In these cases, there is a desire to treat a vessel using a polymer scaffold, in particular a bioabsorbable or bioresorbable polymer scaffold, as opposed to a metal stent, so that the prosthesis's presence in the vessel is temporary.

Polymeric materials considered for use as a polymeric scaffold, e.g. poly(L-lactide) ("PLLA"), poly(D-lactide) ("PDLA"), poly(D,L-lactide-co-glycolide), poly(D-lactide-co-glycolide) or poly(L-lactide-co-D-lactide) with less than 10% D-lactide, poly(L-lactide-co-caprolactone), poly (caprolactone), PLLA/PDLA stereo complex, and blends of the aforementioned polymers may be described, through comparison with a metallic material used to form a stent, in some of the following ways. Polymeric materials typically possess a lower strength to volume ratio compared to metals, which means more material is needed to provide an equivalent mechanical property. Therefore, struts must be made thicker and wider to have the required strength for a stent to support lumen walls at a desired radius. The scaffold made from such polymers also tends to be brittle or have limited fracture toughness. The anisotropic and rate-dependent inelastic properties (i.e., strength/stiffness of the material varies depending upon the rate at which the material is deformed, in addition to the temperature, degree of hydration, thermal history) inherent in the material, only compound this complexity in working with a polymer, particularly, bioresorbable polymers such as PLLA or PLGA.

Scaffolds and stents traditionally fall into two general categories—balloon expanded and self-expanding. The later type expands (at least partially) to a deployed or expanded state within a vessel when a radial restraint is removed, while the former relies on an externally-applied force to configure it from a crimped or stowed state to the deployed or expanded state.

Self-expanding stents are designed to expand significantly when a radial restraint is removed such that a balloon is often not needed to deploy the stent. Self-expanding stents do not undergo, or undergo relatively no plastic or inelastic deformation when stowed in a sheath or expanded within a lumen (with or without an assisting balloon). Balloon expanded stents or scaffolds, by contrast, undergo a significant plastic or inelastic deformation when both crimped and later deployed by a balloon.

In the case of a balloon expandable stent, the stent is mounted about a balloon portion of a balloon catheter. The stent is compressed or crimped onto the balloon. Crimping may be achieved by use of an iris or sliding-wedge types, or other types of crimping mechanisms. A significant amount of plastic or inelastic deformation occurs both when the balloon expandable stent or scaffold is crimped and later deployed by a balloon. At the treatment site within the lumen, the stent is expanded by inflating the balloon. The expanded state is achieved and maintained, substantially, if not entirely by an irreversible or inelastic strain at the crowns of the stent or scaffold caused by the balloon expansion. Self-expanding stents or scaffolds, by contrast, achieve and maintain their expanded state in the vessel by an elastic, radially outward force.

A film-headed crimper has been used to crimp stents to balloons. Referring to FIG. 1A, there is shown a perspective view of a crimping assembly 20 that includes three rolls 123, 124, 125 used to position a clean sheet of non-stick material between the crimping blades and the stent prior to crimping. For example, upper roll 125 holds the sheet secured to a backing sheet. The sheet is drawn from the backing sheet by a rotating mechanism (not shown) within the crimper head 21. A second sheet is dispensed from the mid roll 124. After crimping, the first and second (used) sheets are collected by the lower roll 123. As an alternative to rollers dispensing a non-stick sheet, a stent may be covered in a thin, compliant protective sheath before crimping.

FIG. 1B illustrates the positioning of the first sheet 125a and second sheet 124a relative to the wedges 22 and a stent 100 within the aperture of the crimping assembly 20. As illustrated each of the two sheets are passed between two blades 22 on opposite sides of the stent 100 and a tension T1 and T2 applied to gather up excess sheet material as the iris of the crimping assembly is reduced in size via the converging blades 22.

The dispensed sheets of non-stick material are used to avoid buildup of coating material on the crimper blades for stents coated with a therapeutic agent. The sheets 125a, 124a are replaced by a new sheet after each crimping sequence. By advancing a clean sheet after each crimp, accumulation of contaminating coating material from previously crimped stents is avoided. By using replaceable sheets, stents having different drug coatings can be crimped using the same crimping assembly without risk of contamination or buildup of coating material from prior stent crimping.

There is a continuing need to improve upon methods for crimping a medical device and, in particular, a polymer scaffold to a delivery balloon in order to improve upon the uniformity of deployment of a polymer scaffold from the balloon, to increase the retention force between scaffold and balloon, and to obtain a minimal crossing profile for delivery of the scaffold to a target site.

SUMMARY OF THE INVENTION

The invention provides methods for crimping a balloon-expanded scaffold to a balloon catheter. According to one embodiment the inventive methods disclosed herein are used to improve upon a crimping process for a thin-walled scaffold. The process may alternatively be used to improve-upon a crimp process used to crimp scaffolds that have thicker walls.

Referring to the case of a thin-walled scaffold, it has been realized through testing a need to modify aspects of a crimping process that did not pose significant problems when a higher wall thickness scaffold was crimped using the same process. An example of a scaffold having a higher wall thickness is described in US 2010/0004735. It has been found that when a significant reduction in wall thickness is made (e.g., from 158 microns or about 160 microns wall thickness down to 100 microns wall thickness or less) prior methods of crimping have proven unsatisfactory. Those prior methods of crimping produced high numbers of twisted, cracked or fractured struts when applied to thin-walled scaffolds.

According to the invention, it has been determined that modifications to a crimping process may better ensure that all four of the following objectives are met:

Structural integrity: avoiding damage to the scaffold's structural integrity when the scaffold is crimped to the balloon, or expanded by the balloon.

Safe delivery to an implant site: avoiding dislodgement or separation of the scaffold from the balloon during transit to an implant site and having a small crossing profile for the catheter.

Uniformity of expansion: avoiding non-uniform expansion of scaffold rings, which can lead to structural failure and/or reduced fatigue life.

Avoidance of balloon over-stretch: monitoring of balloon pressure in relation to decreasing scaffold size to avoid excessive strain or possible pin-hole leaks in the balloon and without compromising the three prior needs.

According to the embodiments, a polymer scaffold is crimped to a balloon of a balloon catheter using a crimping device and a crimping barrier or protective sheet, such as a polymer material and hereinafter referred to as a polymer material. The polymer material is disposed between the surfaces of the scaffold and faces of crimper blades that bear down on the scaffold during crimping. In a preferred embodiment the polymer material are sheets provided with a film-headed crimping device. According to this embodiment, the scaffold is crimped down in intermittent fashion. Between one or more crimping stages the polymer sheets are adjusted to remove slack or excess accumulated sheet material. After this re-setting of the polymer sheets the scaffold diameter is reduced down further, which may be followed subsequently by another re-setting of the polymer sheets, as necessary or desired. The number of re-sets of the polymer sheets will in general depend on the degree of diameter reduction during crimping, and more specifically will depend upon the crimping results, type of scaffold being crimped and material of the scaffold.

In an alternative embodiment the polymer material are sheaths placed over the scaffold. According to this embodiment a sheath having a first size is placed over the scaffold. The scaffold diameter is then reduced down by a crimping device. After the scaffold is partially reduced in diameter, the first sheath is replaced by a second, smaller sheath, matching the reduced diameter of the scaffold. The first sheath is replaced by the second, smaller sheath to avoid interference with the crimping process.

In addition to the aforementioned re-set of polymer material during crimping, in some embodiments a crimping process further includes modifying balloon pressurization during crimping to control distribution of balloon material supporting the scaffold. The objective is to maintain a distribution of small folds of balloon material supporting the scaffold during crimping, both when the crimp head is applying pressure to the scaffold and when the aperture is opened to allow for resetting of polymer material. In order to achieve this objective, balloon pressurization adjustment may be needed between times when the crimp blades apply pressure to the scaffold and when the aperture is open.

When balloon material supporting the scaffold inner diameter is distributed predominately as small folds (as opposed to a mixture of small and large folds) the scaffold expands more uniformly when the balloon is inflated. Balloon material formed into mostly or predominately small folds when the scaffold is compressed into it during crimping will subsequently expand out (when inflated) with relatively even radial outward pressure imposed on the scaffold. This relatively even radial outward pressure produces the desired uniformity of expansion.

If instead the scaffold is compressed down onto a balloon with its material formed into a combination of large and small folds, the balloon material when inflated will not apply uniform radial pressure on the scaffold. This is because areas of the balloon with small folds will expand out more quickly than areas with large folds. As a result, one area or region of the scaffold will expand more quickly than another area. An example of this non-uniform expansion is shown in FIG. 7B. The expanded or deployed diameter for the scaffold is the same in either case (with or without even radial pressure applied by the balloon), but the stress distribution among articulation areas of the scaffold is uneven resulting in possible loss of radial strength. Thus, in the case of, for example, application of non-uniform balloon pressure to the pattern shown in FIG. 5, there can be significant over and under expanded scaffold rings producing excessive stresses. Crowns may be strained beyond their yield strength, which can produce a significant loss in radial strength and even failure. One therefore wants to avoid non-uniform expansion of the scaffold for the sake of structural integrity (avoiding fracture or loss of strength in scaffold rings).

If a relatively low balloon pressurization is used during crimping, no balloon pressure adjustments may be needed when crimp blades are removed to reset polymer material. However, if a sufficiently high balloon pressurization is used for crimping, the scaffold may expand outwardly when the crimp blades are withdrawn (a net radial outward force exists on the scaffold when equilibrating radial inward force of crimp blades is removed). It may therefore be desirable to reduce balloon pressure before the crimp blades are removed, so that the scaffold diameter is maintained while the polymer material is reset.

For embodiments where a thin-walled scaffold is crimped, balloon pressure preferably is maintained at a very high level (e.g. near or exceeding a rated burst pressure for the balloon) when the blades are compressing the scaffold (high balloon pressure helps to support scaffold and prevent such events as flipping or twisting of struts from occurring during the diameter reduction). For these embodiments balloon pressure is reduced significantly to avoid expansion of the scaffold when blade pressure is removed. At the same time, a significant amount of balloon pressure must be maintained to ensure that small folds are maintained. It has been found that if the pressure is reduced too much, large folds can form when resetting the polymer material. As explained above, the presence of large folds produces non-uniform expansion of the scaffold. The disclosure provides pressure values to use during resetting of polymer material, relative to or independent of the balloon pressure used when the crimp blades are bearing down on the scaffold.

Although this disclosure primarily refers to the crimping of a scaffold, the scope of the invention is not limited to scaffolds. The disclosure also applies to the crimping of a stent.

According to the various aspects of the invention, there is a medical device, method for crimping, or method for assembly of a medical device comprising such a medical device having one or more, or any combination of the following things (1) through (21):

(1) The medical device is a stent or scaffold crimped to a balloon catheter.
(2) A crimping method applied using a crimping barrier or protective layer, such as a polymer material. The crimping barrier or protective layer is disposed within a crimp aperture and between crimper blades and a scaffold.
(3) Re-setting of a polymer material within an aperture of a crimper head.
(4) A sliding wedge or iris-type crimper is used including but not limited to a film-headed crimper.
(5) The scaffold has a before crimp diameter that is higher than a nominal diameter for the balloon of the balloon catheter to which the scaffold is crimped.
(6) There is at least 2, between 2 and 5 re-sets of polymer material during a crimp process.
(7) There is a dwell period of between 1 and 25 seconds for a stage of a crimping process prior to a final dwell.
(8) A process for crimping a thin-walled scaffold having a wall thickness of less than 125 microns, or less than 100 microns, or between 80 and 125 microns to a balloon.
(9) A scaffold having a pattern according to FIG. 5.
(10) Balloon pressurization during crimping may be higher than a nominal balloon pressure, and balloon pressure decreased (or relieved) after 50%-75% of the final crimp dwell period is complete.
(11) A thin-walled scaffold supported within a crimp head by a balloon inflated to about a rated burst pressure for the balloon, or about 200-250 psi.
(12) Balloon pressure relieved after about 50% to 60% reduction from the before crimping diameter.
(13) A second balloon pressure or P2 during a reset period.
(14) A first balloon pressure or P1 during a diameter reduction and/or dwell period.
(15) Applying a pressure P2 to balloon material so that a shape of balloon material across a circumference facing the luminal surface of a partially crimped scaffold is maintained, about everywhere, complementary to spaces between scaffold struts (the balloon material is complementary when the scaffold was previously radially compressed with balloon pressure P1 applied). The balloon material is complementary to these spaces when a length of a small fold is about a length between struts of the scaffold, about equal to a distance separating adjacent spaces separating struts, or about the width of a strut.
(16) A re-setting of the polymer material takes place according to any combination of the following:
  (a) First re-set takes place after about 30-35% reduction from the before crimp diameter, depending on scaffold initial diameter size (smaller starting size means re-set more likely needed in this range). This re-set may correspond to the time when the scaffold is removed from the crimper and alignment checked (or replacing the balloon with a balloon of a balloon catheter);
  (b) Two or more re-sets may be chosen based on the total travel from initial diameter to final crimp diameter; e.g., for diameter reductions of 2:1 (initial diameter to final diameter) use 2 re-sets, for 3:1 or above 3:1 use 3 or more re-sets;
  (c) For scaffold designs where struts closer together use more resets;
  (d) Employ a re-set whenever there has been a diameter reduction of about 30-35% between stages, but not to exceed in total 2, 3 or 4 re-sets for the entire crimping process; and/or
  (e) Limit to maximum of 5 or between 2 and 5 re-sets. However, more re-sets are certainly possible and may be needed to achieve a desired outcome.
(17) A method, comprising: using a scaffold made from a tube comprising a polymer, the polymer having a glass transition temperature, the scaffold having an outer diameter and the outer diameter having a before crimping size; using a crimping device having a plurality of blades configured to form an aperture, wherein the blades are rotated relative to each other to increase or decrease the size of the aperture during crimping; using a polymer material disposed within the aperture; and crimping the scaffold to the balloon, the crimping comprising: placing the scaffold and balloon within the aperture, wherein the polymer material is between a surface of the scaffold and a surface of the blades, reducing the diameter of the scaffold from the before crimping size to a first size while the balloon has a first pressure, while the scaffold has about the first size and the balloon has a second pressure, resetting the polymer material, reducing the diameter of the scaffold from the about the first size to a second size while the balloon has the first pressure, and while the scaffold has about the second size and the balloon has the second pressure, resetting the polymer material.

(18) The method of (17), (19) or (20) in combination with one or more, or any of items (a)-(l):
 (a) wherein the second pressure is between 3-4 atm or about 50% of a nominal balloon pressure.
 (b) wherein the scaffold is a thin-walled scaffold and the first pressure is about a rated burst pressure for the balloon, or about 200-300 psi.
 (c) wherein the crimping device is a film-headed crimper.
 (d) wherein the polymer material is polymer sheets.
 (e) wherein the polymer material comprises a sheath.
 (f) wherein the scaffold has a crimping temperature during crimping.
 (g) wherein the balloon has a nominal diameter, and wherein the before crimping size is greater than the nominal diameter.
 (h) wherein the crimping step further includes the step of removing the scaffold and balloon from the crimping device after the scaffold diameter is reduced to the first diameter, then returning the scaffold to the crimping device.
 (i) wherein the resetting of the polymer material while the scaffold has about the first size occurs when the scaffold and balloon are removed from the crimping device.
 (j) wherein the balloon is a first balloon, further including the step of replacing the first balloon with a second balloon of a balloon catheter when the scaffold is removed from the crimping device, and the scaffold is crimped to the second balloon.
 (k) wherein the scaffold diameter is reduced from the before crimping diameter to the first diameter using a first crimping device, and the scaffold diameter is reduced from the first size to the second size using a second crimping device.
 (l) wherein the polymer material within the aperture is re-set more than 2 times during the crimping.
 (m) wherein before and after reducing the scaffold diameter from the first size to the second size the aperture is held constant while the balloon has about a nominal diameter.

(19) A method, comprising: using a scaffold made from a tube comprising a polymer, the polymer having a glass transition temperature, the scaffold having an outer diameter and the outer diameter having a before crimping size; using a balloon having a nominal diameter; using a polymer material disposable within the aperture; and using a crimping device having a plurality of blades configured to form an aperture, wherein the blades are rotated relative to each other to increase or decrease a size of the aperture during crimping; and crimping the scaffold to the balloon, the crimping comprising: placing the scaffold and balloon within the aperture, while the balloon has a first pressure, reducing the diameter of the scaffold from the before crimping size to a first size that is between 30% to 35% less than the before crimping size, after reducing the diameter to the first size and while the balloon has a second pressure, increasing the aperture size to remove a pressure of the blades from a surface of the scaffold, followed by removing excess polymer material from the aperture.

(20) A method, comprising: using a scaffold made from a tube comprising a polymer, the polymer having a glass transition temperature, the scaffold having an outer diameter and the outer diameter having a before crimping size; using a balloon having a nominal diameter; using a crimping device having a plurality of blades configured to form an aperture; using a polymer material disposable within the aperture; and crimping the scaffold to the balloon, the crimping comprising: placing the scaffold and balloon within the aperture so that the polymer material is between a scaffold surface and a surface of the blades, reducing the diameter of the scaffold from the before crimping size to a second size, wherein the polymer material within the aperture is reset between 2 and 5 times while the scaffold diameter is reduced from the before crimping size to the second size; and wherein the balloon has a first pressure when the scaffold diameter is reduced in size and a second pressure when the polymer material is reset.

(21) The method of (17), (19) or (20) in combination with one or more, or any of items (a)-(c):
 (a) wherein the polymer material comprises sheaths having different sizes.
 (b) wherein the polymer material are sheets operated by a film-headed crimper.
 (c) wherein the scaffold comprises struts forming rings, wherein neighboring rings are connected to each other by at least two links, and the scaffold is crimped to a theoretical minimum crimp size (D-min).

INCORPORATION BY REFERENCE

All publications and patent applications mentioned in the present specification are herein incorporated by reference to the same extent as if each individual publication or patent application was specifically and individually indicated to be incorporated by reference. To the extent there are any inconsistent usages of words and/or phrases between an incorporated publication or patent and the present specification, these words and/or phrases will have a meaning that is consistent with the manner in which they are used in the present specification.

DETAILED DESCRIPTION

Figure 1A:
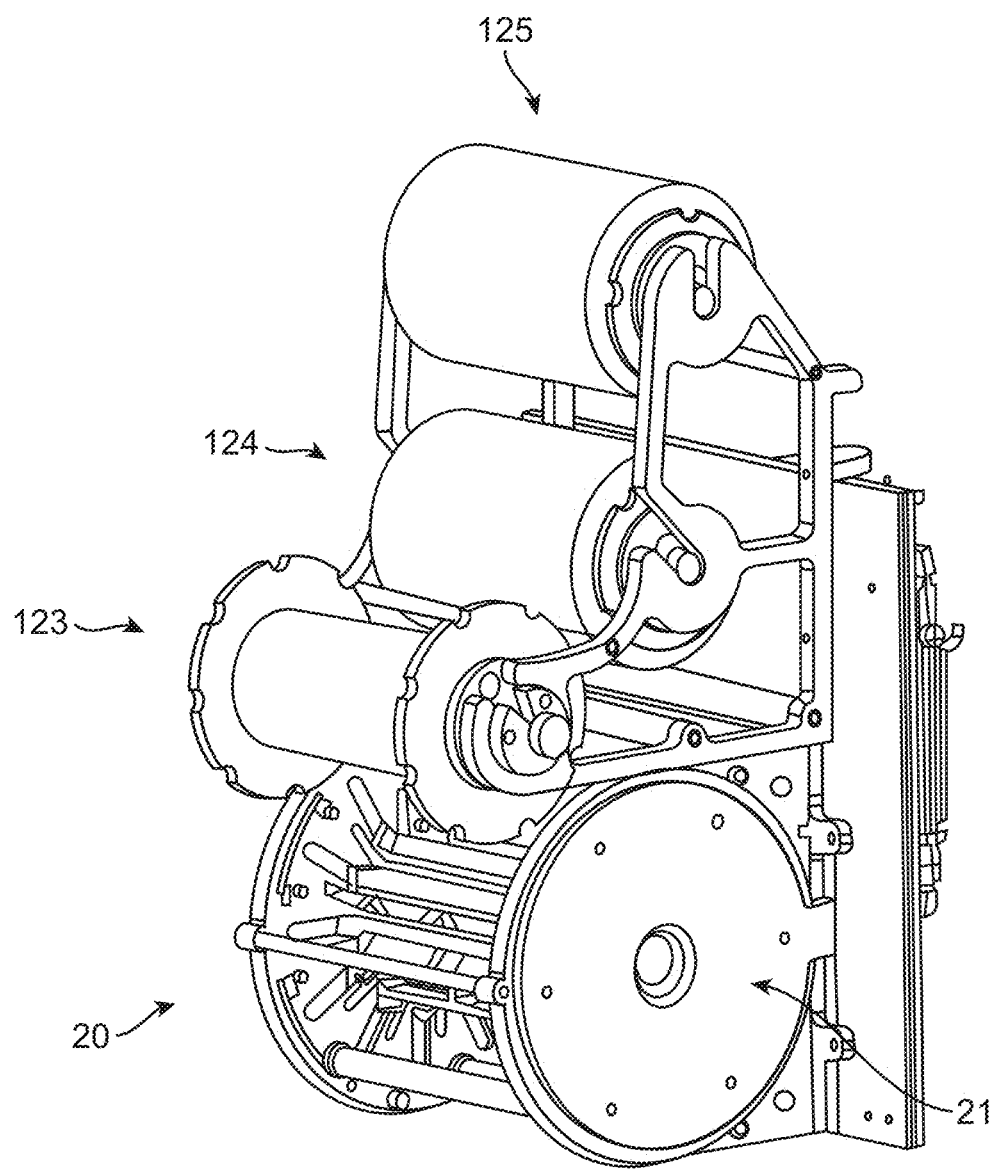
FIG. 1A is a perspective view of a prior art film-headed crimper.

In the description like reference numbers appearing in the drawings and description designate corresponding or like elements among the different views.

For purposes of this disclosure, the following terms and definitions apply:

The terms "about," "approximately," "generally," or "substantially" mean 30%, 20%, 15%, 10%, 5%, 4%, 3%, 2%, 1.5%, 1%, between 1-2%, 1-3%, 1-5%, or 0.5%-5% less or more than a stated value, a range or each endpoint of a stated range, or a one-sigma, two-sigma, three-sigma variation from a stated mean or expected value (Gaussian distribution). For example, d1 about d2 means d1 is 30%, 20%, 15%, 10%, 5%, 4%, 3%, 2%, 1.5%, 1%, 0% or between 1-2%, 1-3%, 1-5%, or 0.5%-5% different from d2. If d1 is a mean value, then d2 is about d1 means d2 is within a one-sigma, two-sigma, or three-sigma variance or standard deviation from d1.

It is understood that any numerical value, range, or either range endpoint (including, e.g., "approximately none", "about none", "about all", etc.) preceded by the word "about," "approximately," "generally," or "substantially" in this disclosure also describes or discloses the same numerical value, range, or either range endpoint not preceded by the word "about," "approximately," "generally," or "substantially."

The "glass transition temperature," TG, is the temperature at which the amorphous domains of a polymer change from a brittle vitreous state to a solid deformable or ductile state at atmospheric pressure. This application defines TG and methods to find TG, or TG-low (the lower end of a TG range) for a polymer in the same way as in US20160081824.

A "stent" can mean a permanent, durable or non-degrading structure, usually comprised of a non-degrading metal or metal alloy structure, generally speaking, while a "scaffold" can mean a temporary structure comprising a bioresorbable or biodegradable polymer, metal, alloy or combination thereof and capable of radially supporting a vessel for a limited period of time, e.g., 3, 6 or 12 months following implantation. It is understood, however, that the art sometimes uses the term "stent" when referring to either type of structure and visa-versa.

"Inflated diameter" or "expanded diameter" refers to the inner diameter or the outer diameter the scaffold attains when its supporting balloon is inflated to expand the scaffold from its crimped configuration to implant the scaffold within a vessel. The inflated diameter may refer to a post-dilation balloon diameter which is beyond the nominal diameter, or nominal inflated diameter for the balloon (e.g., a 6.5 mm balloon has a nominal diameter of 6.5 mm or when inflated to its nominal inflated diameter has a diameter of 6.5 mm). The scaffold diameter, after attaining its inflated or expanded diameter by balloon pressure, will to some degree decrease in diameter due to recoil effects related primarily to, any or all of, the manner in which the scaffold was fabricated and processed, the scaffold material and the scaffold design. When reference is made to a fully inflated diameter of a balloon, it refers to balloon pressurization corresponding to the nominal inflated diameter or greater than the nominal inflated diameter. Balloon pressure may be given in pressure units (e.g., psi or $N/m^2$) or relative to standard atmospheric (abbreviated as "atm"). One atm corresponds to about 14.7 psi or 101325 Pascal or $N/m^2$. Typical balloon inflation pressure tables for balloon catheters have nominal or fully inflated pressures of about between 6-8 atm and have rated burst pressures of about 16 atm.

When reference is made to a diameter it shall mean the inner diameter or the outer diameter, unless stated or implied otherwise given the context of the description.

"Post-dilation diameter" (PDD) of a scaffold refers to the inner diameter of the scaffold after being increased to its expanded diameter and the balloon removed from the patient's vasculature. The PDD accounts for the effects of recoil. For example, an acute PDD refers to the scaffold diameter that accounts for an acute recoil in the scaffold.

A "before-crimp diameter" means an outer diameter (OD) of a tube from which the scaffold was made (e.g., the scaffold is cut from a dip coated, injection molded, extruded, radially expanded, die drawn, and/or annealed tube) or the scaffold before it is crimped to a balloon. Similarly, a "crimped diameter" means the OD of the scaffold when crimped to a balloon. The "before-crimp diameter" can be about 2 to 2.5, 2 to 2.3, 2.3, 2, 2.5, 3.0 times greater than the crimped diameter and about 0.9, 1.0, 1.1, 1.3 and about 1-1.5 times higher than an expanded diameter, the nominal balloon diameter, or post-dilation diameter. Crimping, for purposes of this disclosure, means a diameter reduction of a scaffold characterized by a significant plastic deformation, i.e., more than 10%, or more than 50% of the diameter reduction is attributed to plastic deformation, such as at a crown in the case of a stent or scaffold that has an undulating ring pattern, e.g., FIG. 5. When the scaffold is deployed or expanded by the balloon, the inflated balloon plastically deforms the scaffold from its crimped diameter. Methods for crimping scaffolds made according to the disclosure are described in US20130255853.

A "crimping stage" or "stage" of a crimping process refers to a period of time when the jaws of a crimping device are held fixed, or the aperture of the crimp head is held at a constant diameter. The duration of the stage may be called a dwell period. Dwell periods can range from 1 sec to 25 sec, for initial stages prior to a final dwell. After the final crimped diameter is reached the dwell may be between 50 sec and 300 sec. The aperture of a crimping device is reduced from a first diameter to a second diameter when the crimping device moves from a first stage to a second stage, respectively. The aperture reduction sizes—e.g., from a first diameter or aperture size to second diameter or aperture size—are, for purposes of this disclosure, understood as being the same as the actual outer diameter of the scaffold within the aperture when the scaffold is being reduced in size by the crimper crimp. It is understood, however, that a programmed aperture size may not be exactly the same as the outer diameter of the crimped scaffold size, especially when a scaffold is being crimped to very small diameters.

A material "comprising" or "comprises" poly(L-lactide) or PLLA includes, but is not limited to, a PLLA polymer, a blend or mixture including PLLA and another polymer, and a copolymer of PLLA and another polymer. Thus, a strut comprising PLLA means the strut may be made from a material including any of a PLLA polymer, a blend or mixture including PLLA and another polymer, and a copolymer of PLLA and another polymer.

Figure 5:
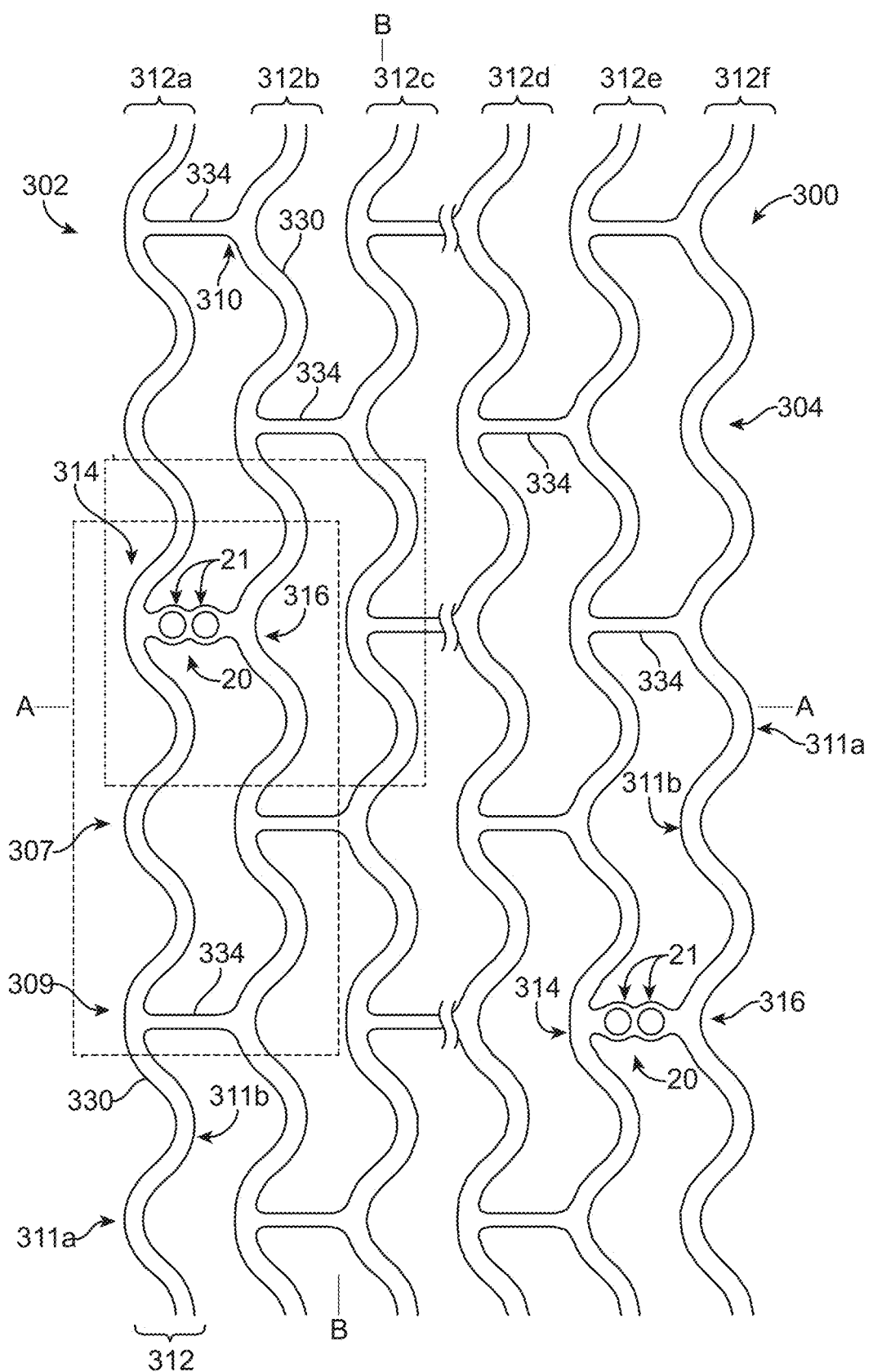
FIG. 5 shows distal and proximal end portions of a scaffold according to one embodiment.

When reference is made to a direction perpendicular to, or parallel with/to axis A-A (e.g., as shown in FIG. 5) it will mean perpendicular to, or parallel with/to the axial direction of a scaffold or tube. Similarly, When reference is made to a direction perpendicular to, or parallel with/to axis B-B (e.g., as shown in FIG. 5) it will mean perpendicular to, or parallel with/to the circumferential direction of the scaffold or tube. Thus, a sinusoidal ring of a scaffold extends parallel with/to (in periodic fashion) the circumferential direction or parallel to axis B-B, and perpendicular to axis A-A whereas a link in one embodiment extends parallel to the axial direction or axis A-A of the scaffold or tube and perpendicular to the axis B-B.

Wherever the same element numbering is used for more than one drawing it is understood the same description first used for the element in a first drawing applies to embodiments described in later drawings, unless noted otherwise.

The dimension of thickness (e.g., wall, strut, ring or link thickness) refers to a dimension measured perpendicular to both of axes A-A and B-B. The dimension of width is measured in the plane defined by axes A-A and B-B; more specifically, the width is the cross-sectional width from one side to another side of a contiguous structure; thus, link 334 can have a constant link width. Moreover, it is understood that the so-called plane of axes A-A and B-B is technically not a plane since it describes surfaces of a tubular structure having central lumen axis parallel with axis A-A. Axis B-B therefore may alternatively be thought of as the angular component if the scaffold locations were being described using a cylindrical coordinate system (i.e., axis A-A is Z axis and location of a luminal/abluminal surface of a crown, link, ring, etc. is found by the angular coordinate and radial coordinate constant).

A "thin wall thickness," "thin-walled scaffold," "thin-wall" refers to a strut, ring, link, or bar arm made from a polymer and having a wall thickness less than 125 microns. The polymer can comprise poly(L-lactide).

A "crimping temperature" according to the disclosure means a temperature above ambient and slightly less than, or about equal to the glass transition temperature (TG) for a polymer of the scaffold, e.g., poly(L-lactide). In a preferred embodiment the crimping temperature is between TG and 15 degrees less than TG, or between TG and 10 degrees, or 5 degrees less than TG. In other embodiments the crimping temperature is achieved by heating the scaffold to a temperature at least 20 degrees below TG and preferably to a temperature at least 15 degrees below TG.

Figure 3A:
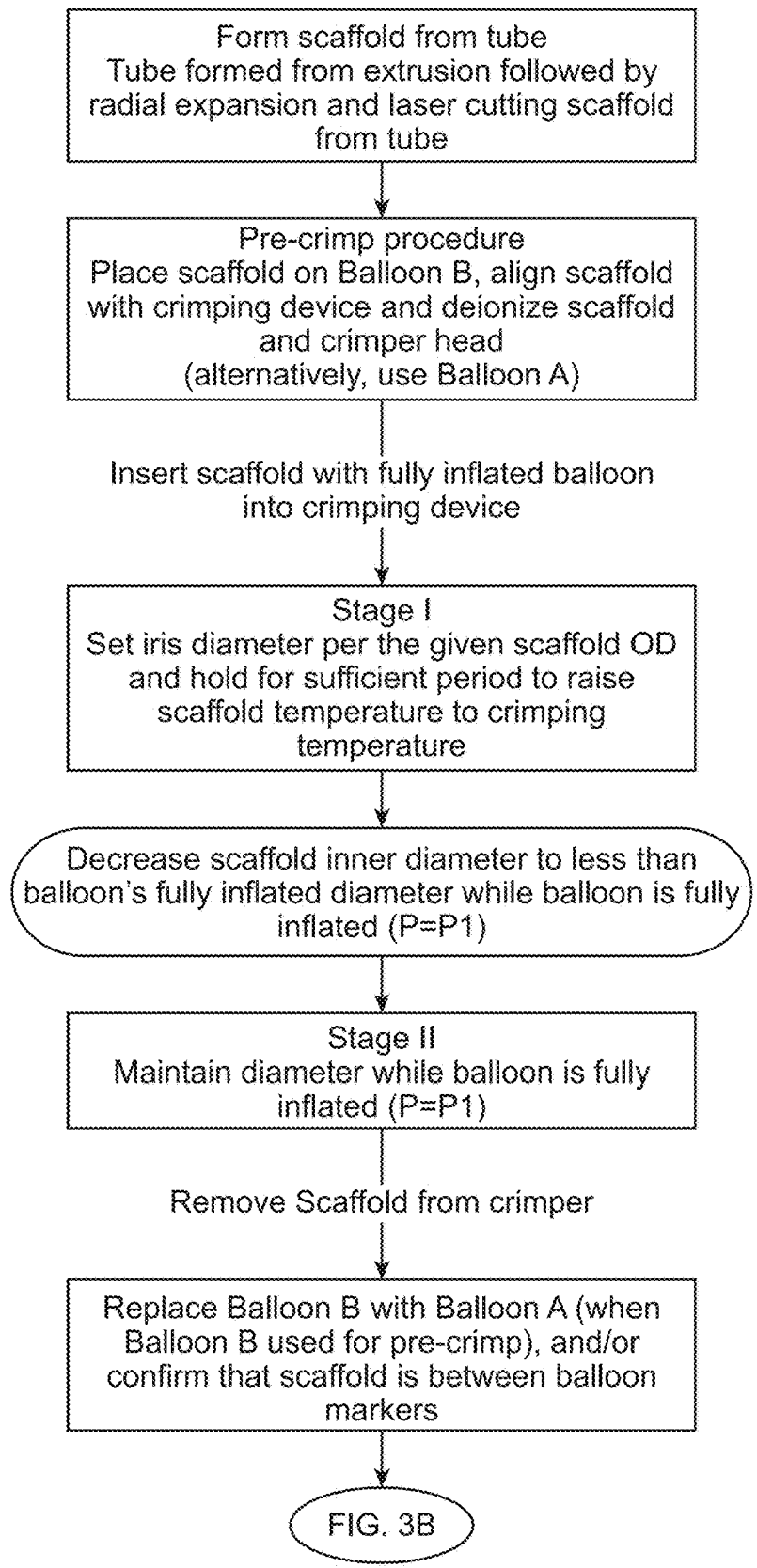
FIGS. 3A and 3B describe a first process (Process I) for crimping a scaffold according to the disclosure.
Figure 3B:
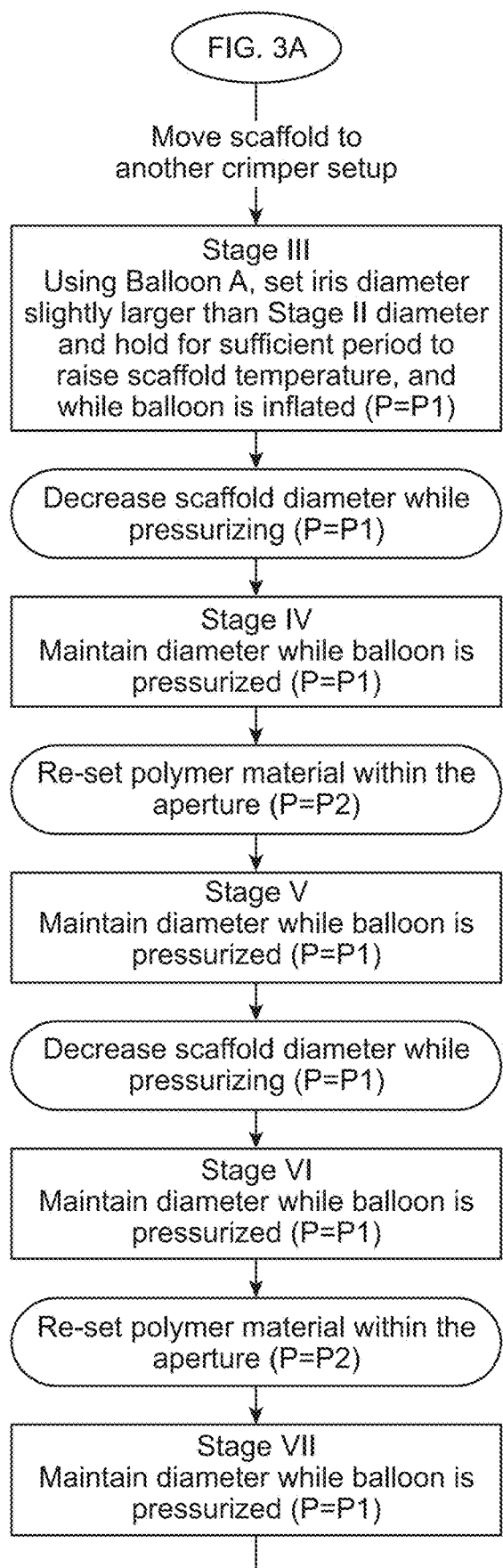
Figure 3B:
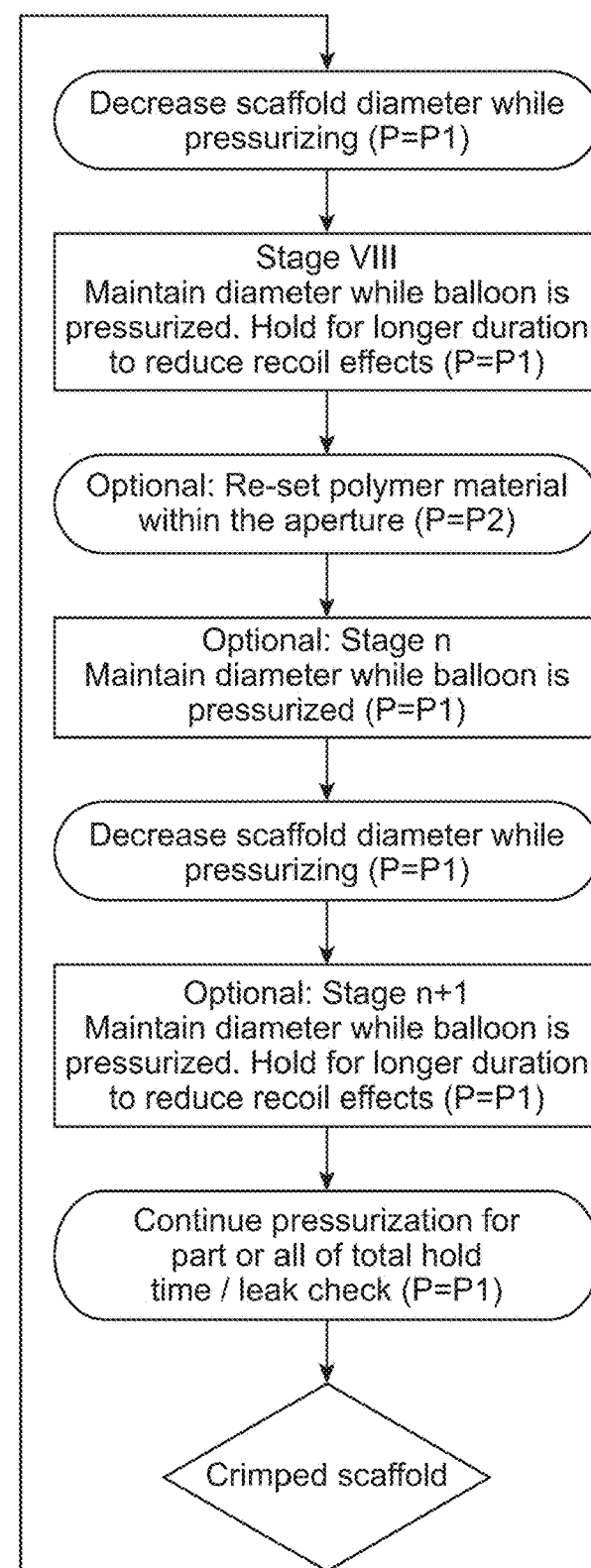
Figure 4A:
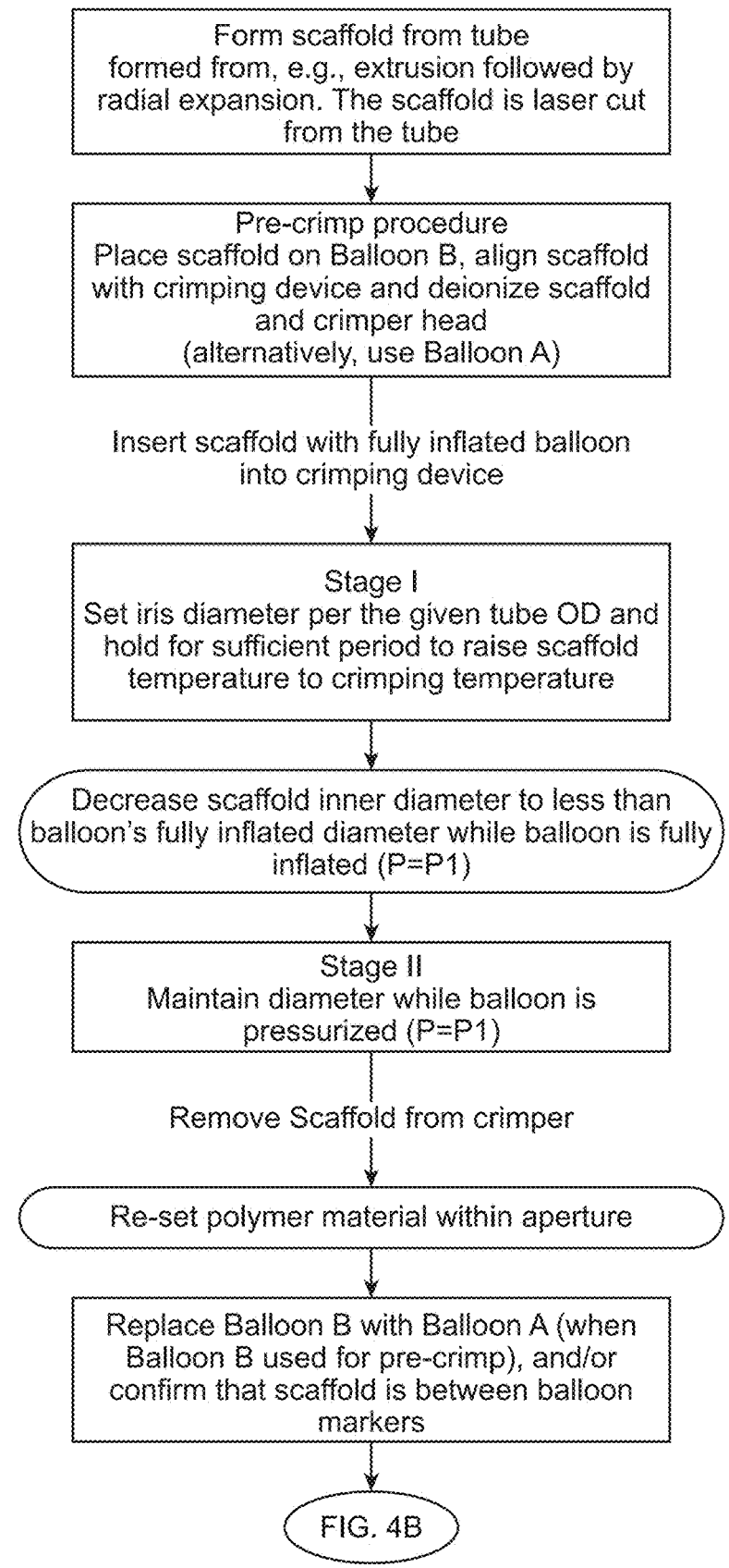
FIGS. 4A and 4B describe a second process (Process II) for crimping a scaffold according to the disclosure.
Figure 4B:
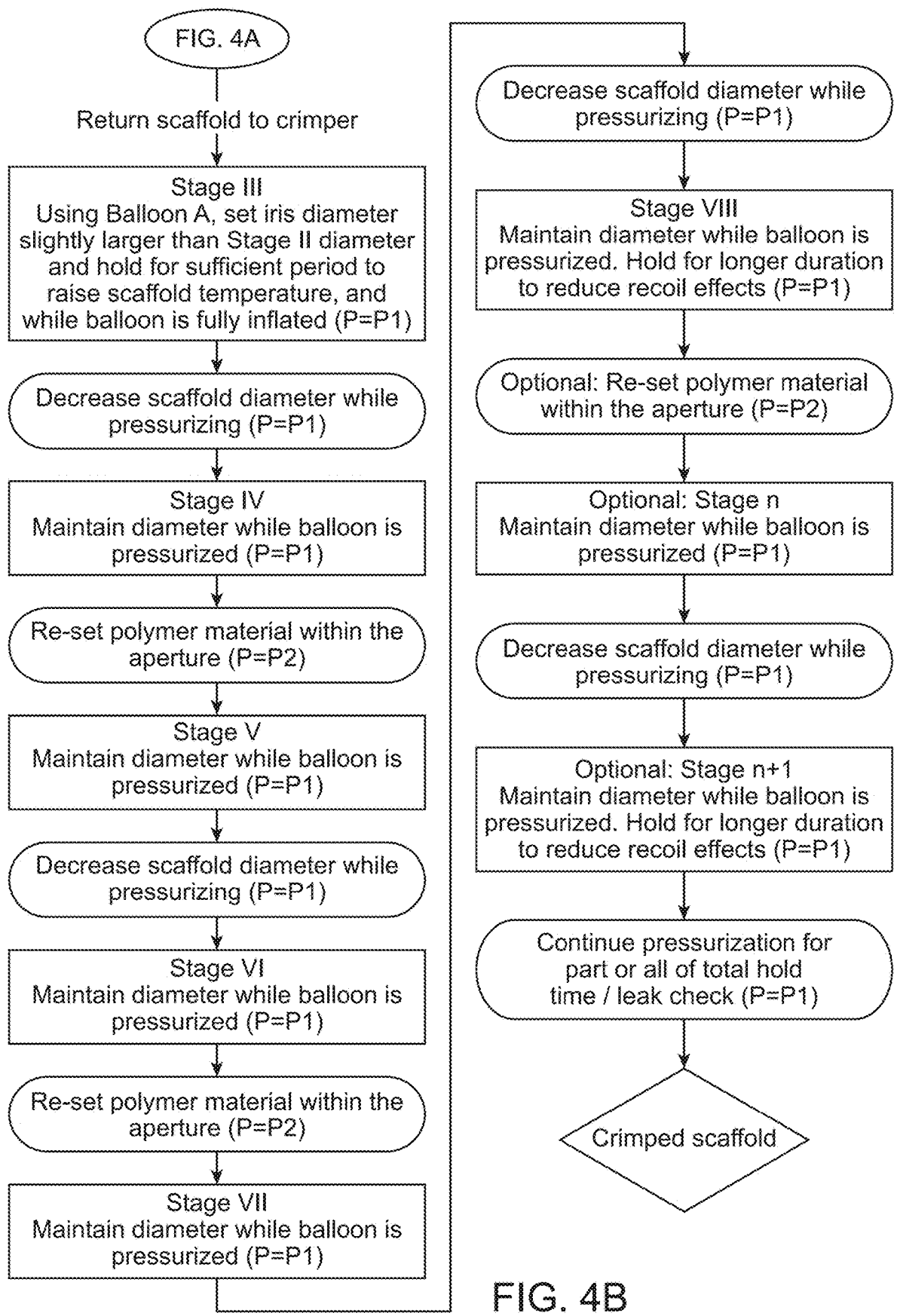

"Re-set of the polymer material within the aperture" as indicated in the crimping steps in FIGS. 3B and 4B or "resetting of the polymer material within the aperture," means one or both of removing excessive polymer material from within an aperture of a crimp head formed by the interconnected blades or wedges of a mechanical crimping device (e.g., an iris or sliding wedge type crimper) or increasing/opening the aperture sufficiently to remove blade pressure on the scaffold (in the case of a film-headed crimper). The blades or wedges converge upon the scaffold in order to reduce the diameter of the scaffold (and crimp the scaffold to the balloon). An example of a film-headed crimper is the MSI™ SC775S/875S, available from the Machine Solutions company. For this crimper re-set of the polymer material within the aperture is accomplished by fully opening the crimp aperture to cause the polymer sheet material to automatically return to its starting position and become fully taut and a fresh sheet of polymer material to spool. After this step, the aperture is then brought back down upon the scaffold to continue the crimping process. A reset of the polymer material can include removing the scaffold and balloon from a crimp head, e.g., as when a first sheath is replaced by a second sheath. Or a reset of the polymer material can take place without removing the scaffold and balloon from a crimp head. For example, in the case of a film-headed crimper the scaffold and balloon are not moved and remain within the crimp head when the aperture is opened, the polymer material is re-set then the aperture is again closed down on the scaffold and balloon.

The term "first pressure" or "P1" shall refer to a balloon pressurization while the scaffold is reduced in diameter size using a crimp head, and/or during a dwell period or when the aperture size is maintained at a constant diameter and restraining outward recoil of the scaffold. P1 can range from between about 3 or 4 atm and up to about a rated burst pressure for the balloon. Preferably P1 is between about 200 psi and 250 psi, or between about 13 atm and 17 atm. In other embodiments P1 is higher than P2, or at least twice the pressure of P2. In a preferred embodiment the scaffold is a thin-walled scaffold and P1 is between about 200 psi and 250 psi, between about 13 atm and 17 atm, or about a rated burst pressure for the balloon in order to provide additional support for scaffold struts as the scaffold rings are being deformed by crimper blades. In other embodiments P1 can range from between about 4 atm and 13 atm.

The term "second pressure" or "P2" shall refer to a balloon pressurization during a reset of the polymer material, and/or when crimp blade pressure is withdrawn or not restraining outward recoil of the scaffold. P2 can be above 1 atm, from above 1 atm to 3 atm, up to about 3 or 4 atm, more than 4 atm and less than P1, or about 50% of a nominal inflation pressure for the balloon.

EMBODIMENTS

An effective crimping process for a scaffold must at least satisfy each of the following objectives:

Structural integrity: avoiding damage to the scaffold's structural integrity when the scaffold is crimped to the balloon, or expanded by the balloon.

Safe delivery to an implant site: avoiding dislodgement or separation of the scaffold from the balloon during transit to an implant site.

Uniformity of expansion: avoiding non-uniform expansion of scaffold rings, which can lead to structural failure and/or reduced fatigue life.

As previously reported in US20140096357 a scaffold is not as resilient as a stent made from metal, which is highly ductile. Satisfying all of the above needs is therefore more challenging for a polymer scaffold, especially a thin-walled scaffold that can fracture more easily during crimping or balloon expansion and is more susceptible to twisting, flipping or overlap during crimping.

According to the disclosure there is a crimping process that includes steps where polymer material is re-set or replaced in the crimp head in order to minimize any interference between the compressing-down of the scaffold struts by crimper blades and the polymer material. The polymer material is used to protect the surface or the scaffold, or coating disposed over a scaffold (or stent). However, as the scaffold is crimped further down and its diameter decreases, the polymer material surrounding the scaffold when it had the larger diameter becomes excessive, resulting in folds, roll-up, slackening or loss of tension. Although a crimping mechanism may include a tensioning portion that applies a tensioning force as the aperture decreases (as a means to take-up excess slack in the polymer material) due to the presence of the blades in close proximity, or in contact with surfaces of the scaffold struts the tensioning force cannot remove material from near the scaffold. To address this problem a crimp aperture is opened and sheet material re-set (or replaced, in case of using sheaths).

Figure 2A:
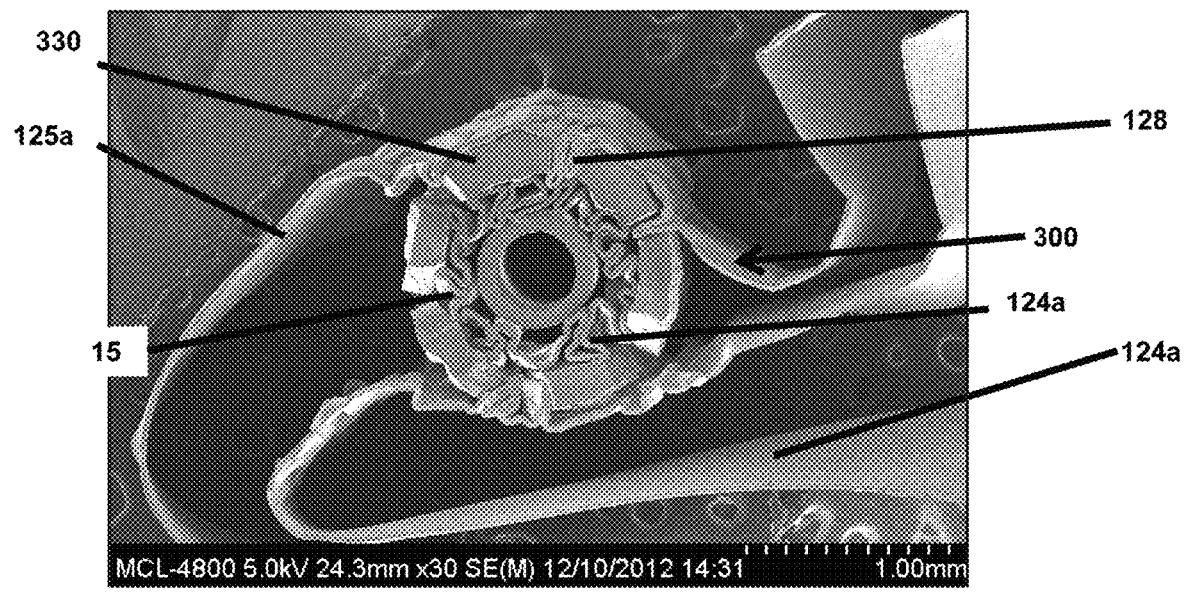
FIGS. 2A-2B are scanning electron microscope (SEM) images of a cross-section of a scaffold partially crimped to a catheter balloon within a crimp head. Polymer sheets of the crimping mechanism are wrapped around the scaffold with portions lodged between scaffold struts.
Figure 2B:
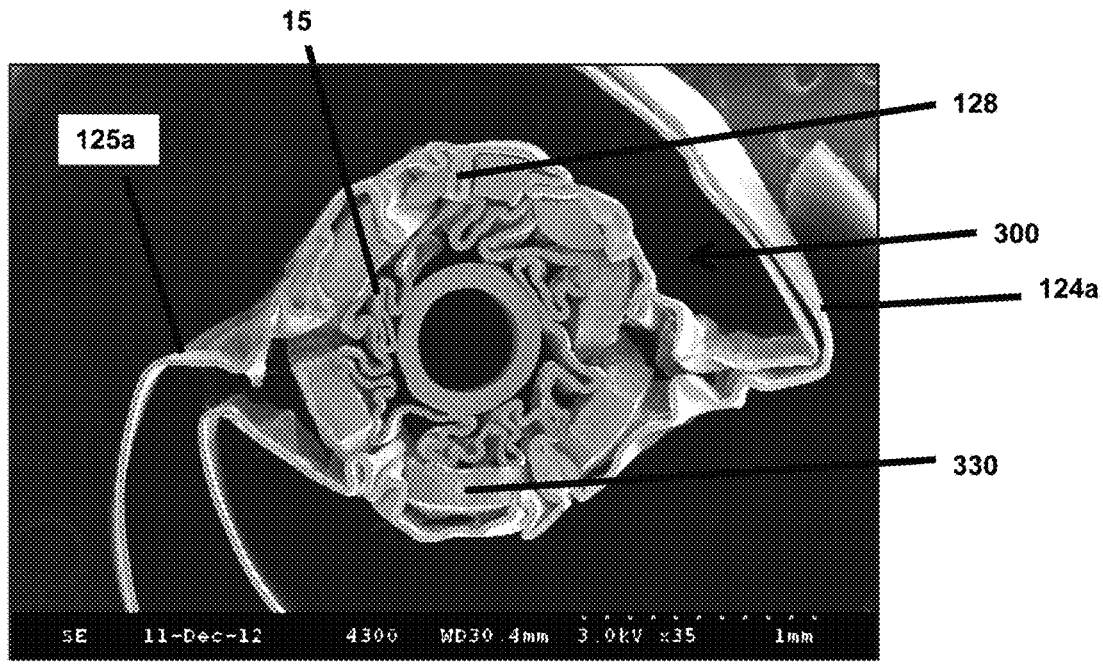

FIGS. 2A-2B illustrates what happens when polymer sheet material becomes slack when the diameter and blades are not removed to re-set the sheets, or the sheets are not otherwise kept relatively taut near the scaffold surface. Shown is the inside of the crimp head of a film-headed crimper. Although the film-headed crimper includes the tensioning mechanism mentioned above, sheet material nonetheless becomes lodged between struts of the scaffold because the blades' proximity to the scaffold surface limits the effectiveness of the tensioning mechanism. Basically, during a crimp stage, or diameter reduction between stages, the blades are pressing down on the scaffold surface, or the blades are very near the scaffold surface, thereby restraining movement of the polymer material disposed between the blades and scaffold surface when tension is applied to the sheet material portions outside of the aperture. The tension applied outside the blade is reacted by a pinching force on the polymer material resulting from polymer material being pinched between the blade and scaffold. As shown the scaffold 300 (partially crimped to balloon 15) has struts 330. Portions 128 of the sheets 124a/125a are caught between the folding struts 330. As these struts attempt to fold about crowns, thereby reducing ring sizes and diameter of the scaffold, the slack polymer material 128 is drawn or pushed into open spaces between struts by the converging blades. This can be easily seen in FIGS. 2A-2B. Particularly for thin-walled scaffold struts, excessive interaction of the pinched sheets with the folding struts tends to result in unsatisfactory crimped units.

Re-setting or removal of the excessive polymer material after diameter reductions (by withdrawing the blades or increasing the aperture size, in order to allow the outside tensioning to pull the polymer material away from the scaffold surface) was found to make a significant difference in the quality of crimp and production yields. It was found through testing and experimentation that a re-set or removal of excessive polymer sheet material (or in the alternative embodiment replacing a first sheath with a second, smaller sheath) at critical times (as explained below), following a diameter reduction, can prevent the polymer material from significantly interfering with the desired folding of ring struts about crowns in subsequent diameter reduction steps.

Figure 1B:
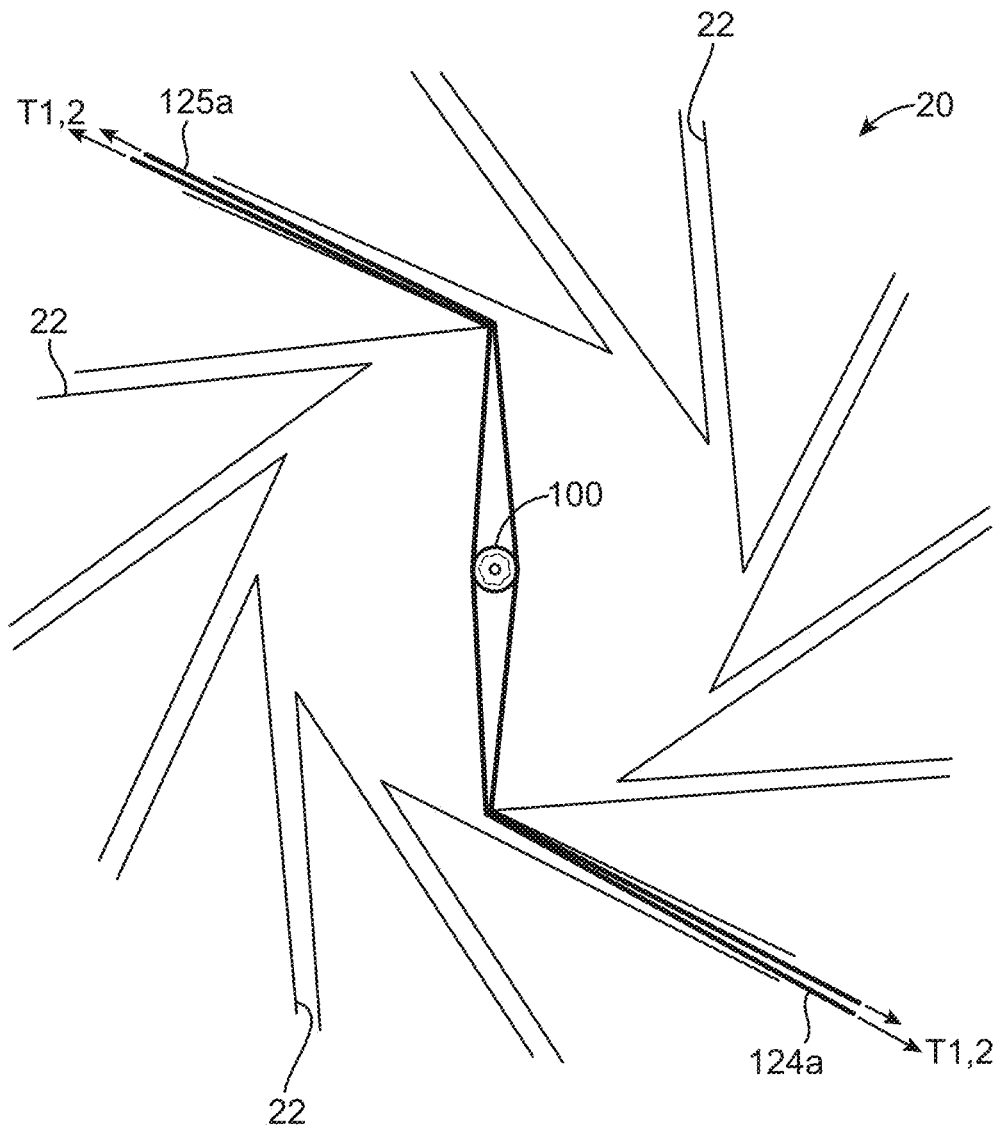
FIG. 1B is a frontal view of the head of the film-headed crimper of FIG. 1A as crimper jaws are being brought down on a stent.

As discussed earlier in reference to FIG. 1B, for the film-headed crimper a first sheet 125a and a second sheet 124a are positioned relative to the wedges or blades 22 of the crimping device while the scaffold (or stent 100) is within the aperture of the crimping assembly 20. The two sheets are passed between two blades 22 on opposite sides of the stent 100 and a tension T1 and T2 applied to gather up excess sheet material as the iris of the crimping assembly is reduced in size via the converging blades 22. Although this tensioning mechanism is intended to keep the sheets relatively taut, the sheet material nonetheless builds up in an unacceptable manner, as explained above.

Figure 7A:
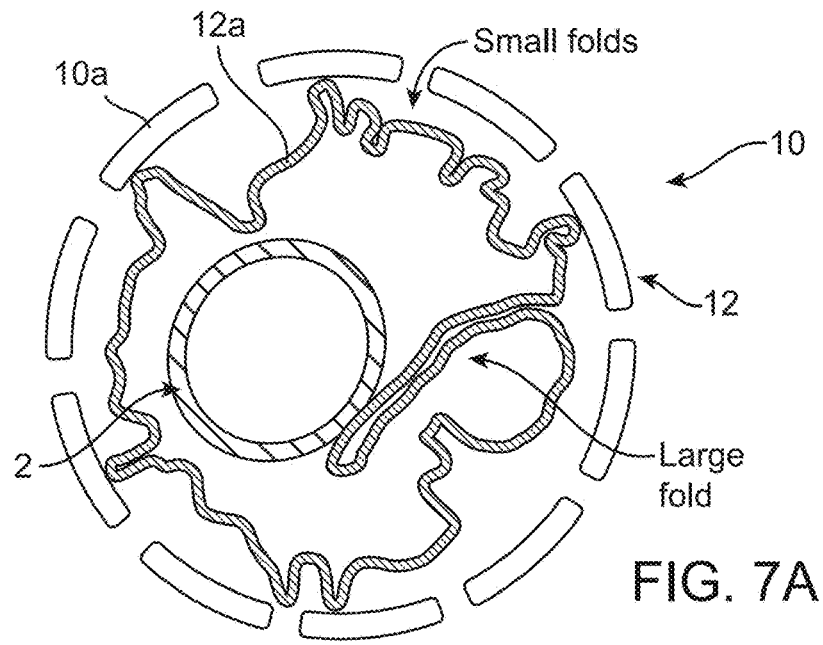
FIG. 7A is a cross sectional view of a scaffold partially crimped to a balloon of a balloon catheter. The drawing depicts the presence of large folds and small folds of balloon material when pressure to the balloon interior is discontinued.
Figure 7B:
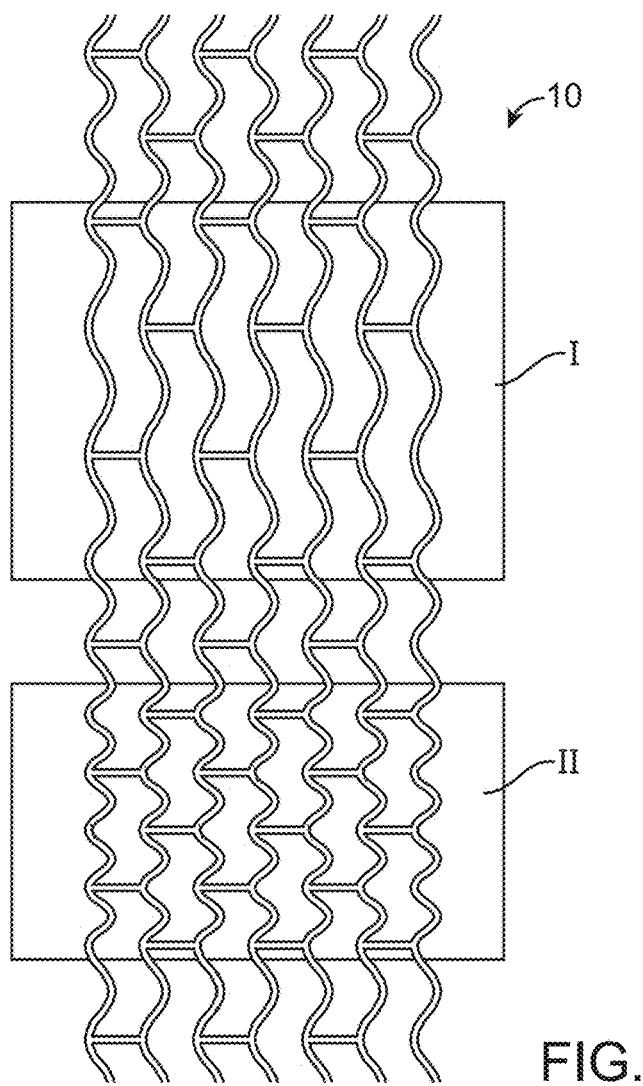
FIG. 7B is a planar view of the scaffold from FIG. 7A after radial expansion from a crimped state using the balloon. The scaffold was crimped with re-set periods taking place without pressure supplied to the balloon interior. As a result, the balloon material took a shape similar to that shown in FIG. 7A during the re-set periods. As can be seen in FIG. 7B, there is non-uniform unfolding or deployment of the rings of the scaffold (compare Region I to Region II in FIG. 7B). This non-uniform deployment from the crimped to expanded state (FIG. 7B) is caused by uneven radial pressure applied by the balloon to the scaffold struts when the balloon is being inflated. This uneven deployment is believed to be caused by the presence of large folds (FIG. 7A) when the scaffold is fully crimped to the balloon.

FIG. 7A is a cross sectional view of a scaffold 10 partially crimped to a balloon 12 of a balloon catheter 2 when a pressure less than P2 is applied to the balloon 12. The drawing depicts the presence of a large fold and small folds of balloon material 12a. FIG. 7B shows the scaffold 10 after it has been expanded using the balloon 12 having the large fold in FIG. 7A. The large fold (when present beneath the fully crimped scaffold) causes a region of the balloon to expand at a different rate than regions of the balloon that have the small folds. As a consequence of this irregular expansion, a non-uniform radial-outward pressure is applied to the balloon resulting in the expanded scaffold pattern. Section II of the scaffold receives less radial outward pressure than desired, while Section I of the scaffold receives more radial outward pressure than desired. Or, alternatively, Section II elements, e.g., crowns, of the scaffold network do not arrive at the level of strain that the crowns are designed to take, whereas the Section I elements exceed this design strain. The net result is the intended expanded diameter, but at the cost of overstraining elements in Region I. Thus, crowns of rings in Region I are potentially prone to loss of strength or failure when the scaffold is implanted in a vessel and subjected to cyclic radial loads.

Figure 8A:
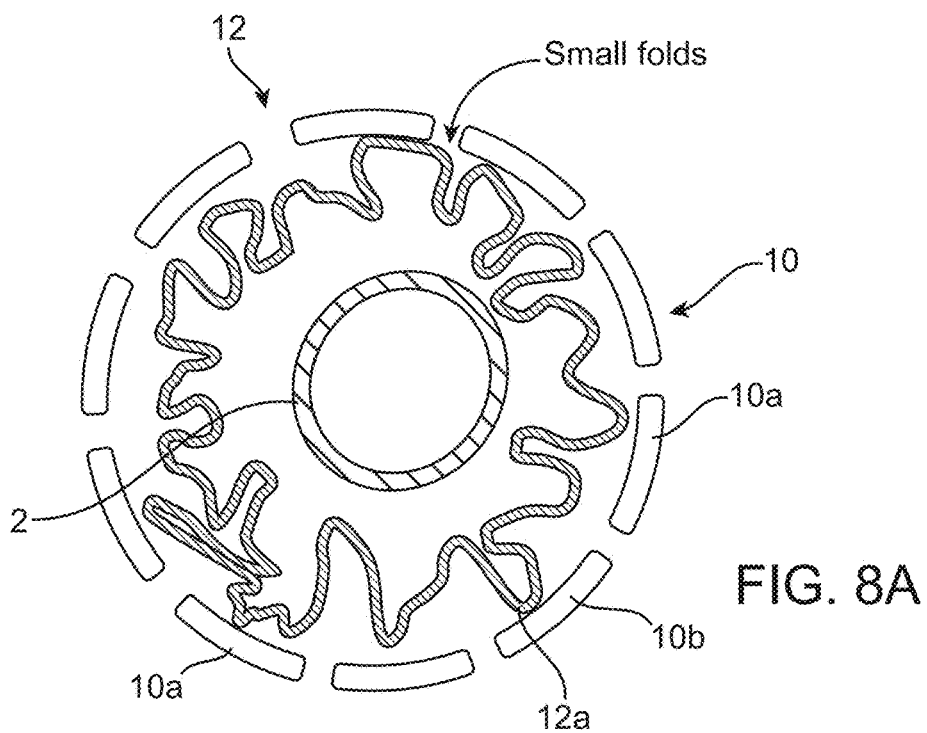
FIG. 8A is a cross sectional view of a scaffold partially crimped to a balloon of a balloon catheter where balloon pressure is maintained when the crimp blade pressure is removed for resetting polymer material. The drawing depicts the presence of small folds, or absence of large folds of balloon material when pressure inside the balloon is significantly higher than the balloon's interior pressure in FIG. 7A. The balloon interior pressure depicted in FIG. 8A is well above 1 atm. For example, the balloon interior pressure is between about 3 atm and 4 atm.

FIG. 8A is a cross sectional view of the scaffold 10 partially crimped to the balloon 12 of the balloon catheter 2 where balloon pressure P2 is applied to the balloon 12. The drawing depicts the presence of small folds or absence of large folds. Balloon material 12a takes a shape complementary to spaces between scaffold struts 10a, 10b and partially enters these spaces during crimping. The length of a small fold is about equal to the length of a strut (in contrast to the length of the large fold depicted in FIG. 7A). A fold length may be thought of as the distance between consecutive folds in material 12a. Importantly, there is much less variation in, or a narrower range of fold lengths of the balloon material 12a in FIG. 8A than in the case of FIG. 7A. It was found that without P2 applied the folding of balloon material 12a would be non-uniform as in FIG. 7A.

In some embodiments balloon material is complementary to spaces between struts when a length of a small fold is about a space between struts of the scaffold, such as a balloon fold length is about equal to the distance from a first strut to a third strut, and there is a second strut between the first strut and the third strut, or in the example of FIG. 8A, the fold is about equal to a width of a strut 10a, or distance from a first space to an adjacent space separating struts. This complementary balloon material was not present if the pressure was not at least P2 and if the pressure was too high the balloon pressure would expand the scaffold.

Figure 8B:
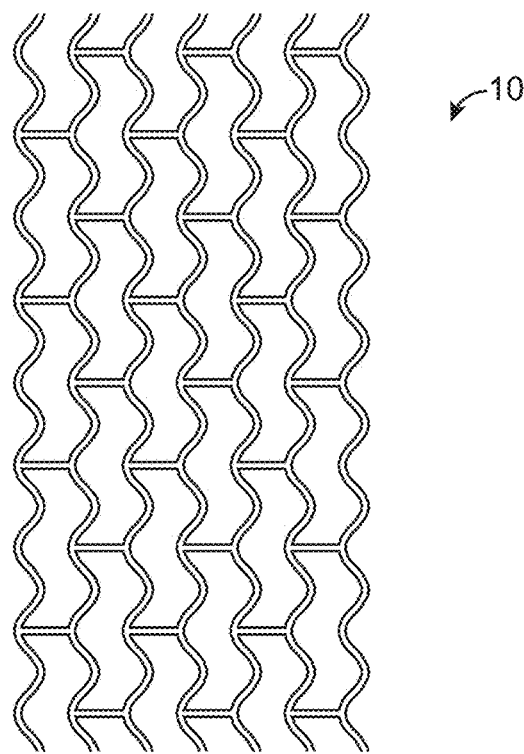
FIG. 8B is a planar view of the scaffold from FIG. 8A after radial expansion from a crimped state by inflating the balloon. The scaffold depicted in this drawing was crimped with re-set periods taking place while pressure is supplied to the balloon, e.g., between about 3 atm and 4 atm during a reset period.

FIG. 8B is a planar view of the scaffold 10 from FIG. 8A after radially expansion from the crimped state using the balloon 12. The scaffold depicted was crimped with pressure P2 applied during re-set periods. As compared to FIG. 7B, there is uniform deployment. There are no regions of the scaffold that are over or under the design strain.

FIGS. 3A, 3B (Process I) and FIGS. 4A, 4B (Process II) are flow diagrams illustrating two examples of crimping processes that can achieve the foregoing objectives for scaffolds, including thin-walled scaffolds. In each of these examples the scaffold crimped to the balloon is laser cut from a radially expanded tube. However, the crimping process is not limited to a scaffold made from a laser-cut tube. Other scaffold types, e.g. a scaffold not radially expanded, or scaffolds fabricated from a polymer sheet (as opposed to a tube) are within the scope of disclosure. Additionally, the starting outer diameter sizes for the scaffold, e.g. a coronary scaffold, can be between 3.0 mm and 4.25 mm or between 2.0 mm and 6 mm. For a peripheral scaffold a starting outer diameter size can be between 6 mm and 10 mm.

Crimping Processes I and II may use one or two balloons. The two balloons referred to in the figures and below discussion are called "Balloon A" and "Balloon B." The Balloon A refers to the balloon of the balloon catheter of the finished product. The Balloon B refers to a temporary or sacrificial balloon, or balloon catheter that is used during the initial stages then replaced by the Balloon A at the time of a final alignment check, as explained below. Practice of the Process I or Process II using Balloon B (later replaced by Balloon A) is desirable when the starting inner diameter size of the scaffold is larger than, or the same size as the diameter of the Balloon A when Balloon A is inflated to its nominal inflation diameter, or when Balloon A is inflated beyond this size.

In a preferred embodiment of a crimping process a film-headed crimper is used to crimp the scaffold to the balloon catheter. For a film-headed crimper, polymer material in the form polymer sheets dispensed from a pair of rolls (FIGS. 1A-1B) is used to protect the scaffold from the blades of the crimper. Thus for this type of crimper "the re-set of polymer material within the aperture" steps means the process of opening the aperture to cause automatic removal of excessive polymer sheet material from the aperture and re-tensioning of the polymer sheets. It will be understood, however, that the invention is not limited to using a film-headed crimper, and may be practiced by alternative arrangements for placing and removing or re-setting of polymer material within the crimp aperture, e.g., using multiple sheaths.

Referring to FIGS. 3A-3B (Process I), two crimper settings or setups are used. The first crimper setup is used for the crimping stages that precede a final alignment check (FIG. 3A) and the second crimper setup is used for the stages that follow the final alignment check (FIG. 3B).

Pre-Crimp Procedure:

The scaffold is placed on Balloon A (or Balloon B if two balloons will be used). The balloon is inflated to its nominal diameter or post-dilation diameter (greater than nominal diameter size) or, more generally, the balloon is fully inflated so that its size is at least equal to or exceeds the inner diameter of the scaffold in order to support the scaffold during the initial crimping steps. The scaffold is aligned with proximal and distal markers on the balloon (not necessary if Balloon B is used). The crimper head, scaffold and/or balloon may also be deionized to remove static charge buildup that can cause the scaffold to shift out of alignment with balloon markers during crimping. Static charge buildup has been found to not only cause misalignment between the scaffold and balloon, but also cause irregular crimping of the scaffold (metal stents typically do not have static charge buildup because the balloon is in sliding contact with a metal, as opposed to a polymer surface). The scaffold is then inserted into the crimper head while the balloon remains fully inflated.

Stage I:

The scaffold supported on the fully inflated balloon is within the crimp head. The temperature for crimping or crimping temperature is set during this stage, as is the starting iris or aperture size corresponding to the input outer diameter of the scaffold (e.g. 3.5 mm). In a preferred embodiment blades of an iris or sliding wedge crimping device are heated to achieve the desired crimping temperature (alternatively a heated liquid or gas may be used). After the scaffold reaches the crimping temperature, the iris of the crimper closes to reduce the scaffold inner diameter (ID) to less than the outer diameter (OD) of the fully inflated balloon and while the balloon has pressure P1.

Stage II:

The crimper jaws are held at a fixed diameter for a dwell period and while the balloon has pressure P1. At the conclusion of this dwell period the scaffold and balloon are removed from the crimping device. The balloon may have a pressure of P2 when removed from the crimping device.

Verify Alignment/Replace Balloon:

Removal after Stage II may be skipped if there is no need to check or verify final alignment with balloon markers, or if Balloon A is used for Stages I and II. In the illustrated embodiment the scaffold supported on the balloon is removed from the crimping device to verify that the scaffold is located between the balloon markers (when Balloon A used for Stages I and II), or Balloon B is replaced with Balloon A and the scaffold aligned with the balloon markers.

Referring now to FIG. 3B, Process I continues. The crimping steps illustrated in FIG. 3B use a crimping setup different from the crimping setup in FIG. 3A.

Stage III:

After the scaffold and inflated Balloon A are returned to the crimper, the iris diameter is set at a slightly higher diameter than the scaffold diameter at the conclusion of Stage II (to account for recoil). The iris or aperture size is held constant for a time period sufficient to bring scaffold temperature back to crimping temperature.

After the crimping temperature is reached, the scaffold diameter is reduced down while the balloon has pressure P1. The balloon has pressure P1 for the diameter reduction following Stage III.

Stage IV:

The crimp aperture is held constant for a dwell period after scaffold diameter is reduced from the Stage III diameter and the balloon has pressure P1. Following Stage IV the polymer sheets of the film headed crimper are re-set to remove excess sheet material from within the aperture when the scaffold diameter was reduced from the Stage III diameter to the Stage IV diameter, or when the diameter was reduced from the initial diameter to the Stage IV diameter. The balloon has pressure P2 when the polymer material is reset.

Balloon pressurization in the crimping process helps ensure, or improves scaffold retention on the balloon, in addition to helping promote uniform expansion of the balloon. Balloon pressure may be relieved after 50%-75% of a final crimp dwell period is complete. Typically 75-250 psi is applied when reducing the scaffold diameter (or stent diameter) and during dwell periods, or more preferably pressure between about 200-250 psi, between about 200-280 psi, and between about 200-300 psi when crimping a thin-walled scaffold. The pressure is selected to achieve the lowest possible crossing profile, ensure sufficient retention and provide radial support for the scaffold struts when rings are being folded by the crimper blades.

Stages V-VIII:

These stages follow a similar process as in Stages III-IV: perform a dwell at each of the stages with a diameter reduction between the stages while the balloon has a pressure P1. After the dwell period, the aperture is fully opened and the excess polymer sheet material removed from the aperture while the balloon has a pressure P2. In total there are three illustrated re-sets of the polymer material in the example of FIGS. 3A-3B. The re-sets all occur following the final alignment check.

Optional Stages/Final Crimp:

Following the re-set (immediately after Stage VIII) there may be a number of additional, optional stages. At the conclusion of these stages there is a final pressurization of the balloon at the final crimp diameter and with balloon pressure P1. The pressurization may be a leak check. After this final step the scaffold is fully crimped to the balloon catheter, removed from the crimp head and placed within a constraining sheath.

FIGS. 4A-4B (Process II) describe an alternative crimping process. The description accompanying FIGS. 3A-3B applies in the same manner to FIGS. 4A-4B, except as follows. A different crimper device or setup is used for Process I after the final alignment check. Step III through Step VIII in Process I is performed on a different crimper device or setup. A re-set of the polymer material therefore may be automatically done at the time of the final alignment check in Process I (after Stage II and before Stage III). This is why a re-setting of polymer material within aperture is not shown in FIG. 3A. In Process II a single crimping device or setup (recipe) is used for the crimp. At the conclusion of Stage II of Process II (FIG. 4A) the polymer material is re-set. The re-set may be done before or after the alignment check and/or changing of balloons (when Balloon B is used for Stage I and Stage II), assuming the final alignment check is even done (this step is optional in some embodiments). Process I and Process II have a total of four illustrated steps where polymer material within the aperture is re-set. For Process I there may be an additional re-set step that is essentially done when the second crimping device/setup is used following the alignment check (thus, bring total of 4 re-sets for Process I). The number of re-sets for a particular scaffold size, balloon size and associated D-min (defined below) is chosen in an optimal fashion, based on examination of the scaffolds crimped to balloons. The criterion used to judge the effectiveness of a selected number of re-sets was the foregoing three listed objectives for crimping (structural integrity, scaffold retention and uniform expansion). It will be appreciated that polymer material interference with strut folding, especially the kind illustrated in FIGS. 2A-2B, can negatively affect any, or all three of the crimping objectives. Balanced against the desire to re-set polymer material is the time needed to re-set and output yield benefits.

According to one embodiment, a re-set of the polymer material should be employed whenever the space between struts is large enough to receive sheet material (near final crimp diameters spaces between struts may be too small for sheet material) and there has been a sufficient percentage of diameter reduction to cause material between the blades and scaffold surface to build up. This period of diameter reduction and resulting crimp size will be referred to as a critical crimping period.

The number of re-sets cannot be excessive because then the crimp process becomes too time consuming. Thus, it is not believed feasible or cost-effective to implement a re-set whenever the scaffold is reduced in diameter. A balance is needed. Re-set points within critical crimping periods should be chosen so that production yield is favorable but crimp time does not become overly burdensome.

Based on extensive testing of different scaffold types, critical crimp periods may employ one or more re-set of polymer material within the aperture ("re-set") according to one or more of the following rules:

A first re-set employed after about 30-35% reduction from the initial diameter, depending on scaffold initial diameter size (smaller starting size means re-set more likely needed in this range). This re-set may correspond to the time when the scaffold is removed from the crimper and alignment checked (or switching to Balloon A);

Two or more re-sets may be chosen based on the total travel from initial diameter to final crimp diameter; e.g., for diameter reductions of 2:1 (initial diameter to final diameter) use 2 re-sets, for 3:1 or above 3:1 use 3 or more re-sets;

For scaffold designs where struts closer together use more resets;

Employ a re-set whenever there has been a diameter reduction of about 30-35% between stages, but not to exceed in total 2, 3 or 4 re-sets for the entire crimping process; and/or Limit to maximum of 5 or between 2 and 5 re-sets. However, more re-sets are certainly possible and may be needed to achieve a desired outcome.

Figure 6:
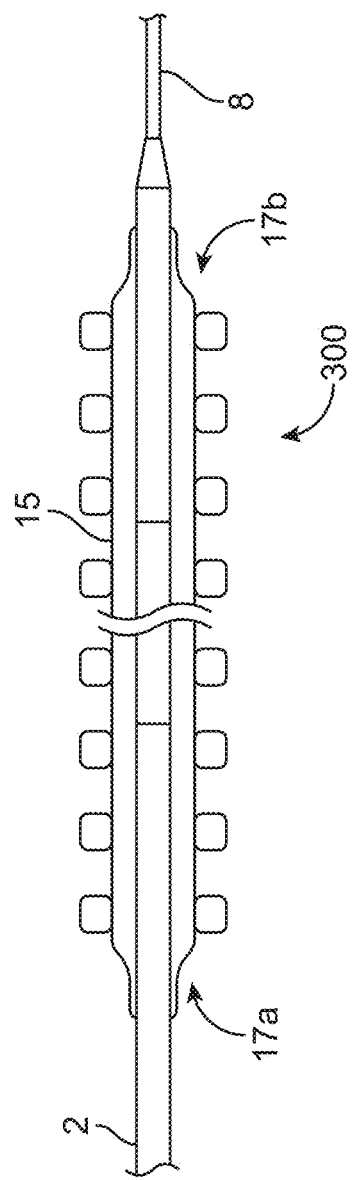
FIG. 6 shows the scaffold of FIG. 5 crimped to a balloon of a balloon catheter.

FIG. 6 illustrates a side-view of a scaffold 300 crimped to a balloon catheter, which has a shaft 2, balloon 15 with distal and proximal ends 17a, 17b (where balloon markers are found). The catheter is supported on a mandrel 8.

FIG. 5 shows a partial, planer view of end portions of the scaffold 300 from FIG. 6 in an expanded or before-crimping state. This figure illustrates an example of a network of struts and links for the scaffold 300. The left or distal end portion 302 (i.e. the left side of FIG. 5) includes sinusoidal rings 312a, 312b, and 312c where ring 312a is the outermost ring. Ring 312a and ring 312b are adjoined by two links 334 and a marker link 20. Ring 312d and ring 312e are adjoined by three links 334 that extend parallel to axis A-A. The links 334 extend parallel to axis A-A and have a constant cross-sectional moment of inertia across its length, meaning link 334 has a constant width and thickness and the location of the centroid or geometric center (or longitudinal axis) of the link is parallel with axis A-A. The right or proximal end portion 304 (i.e. the right side of FIG. 5) includes sinusoidal rings 312d, 312e, and 312f where ring 312f is the outermost ring. Ring 312d and ring 312e are adjoined by three links 334. Ring 312e and ring 312f are adjoined by two links 334 and the marker link 20. Thus, scaffold 300 has a marker link 20 extending between and adjoining the outermost link with the adjacent, inner ring. The scaffold 300 may have 15-20, e.g., 15, 18 or 20 rings 312 interconnected to each other by links 334.

A ring 312, e.g., ring 312b, can be sinusoidal meaning the curvature of the ring along axis B-B is best described by a sine wave where the wavelength of the sine wave is equal to the distance between adjacent crests 311a of the ring. The ring can have a constant width at both crowns 307, 309 and 310 and struts 330, which connect a crown to an adjacent crown.

There are three crown types present in each inner ring 312b through 312e: U-crown, Y-crown and W-crown. Outermost rings have only the Y-crown or W-crown type, and the U-crown type. A crest or peak 311a (or trough or valley 311b) may correspond to a U-crown, Y-crown or W-crown. For the outermost ring 312a there is only a U-crown and W-crown type. For the outermost ring 312f there is only a U-crown and Y-crown type. A marker link 20 adjoins rings by forming a W-crown with the first ring (e.g., ring 312e) and a Y-crown with the second ring (e.g. ring 312f).

A link 334 connects to ring 312f at a Y-crown 310. A "Y-crown" refers to a crown where the angle extending between a strut 330 of a ring 312 and the link 334 is an obtuse angle (greater than 90 degrees). A link 334 connects to ring 312a at a W-crown 309. A "W-crown" refers to a crown where the angle extending between the strut 330 and the link 334 is an acute angle (less than 90 degrees). A U-crown 307 is a crown that does not have a link connected to it. Marker link 20 connects to a ring at a W-crown 314 and a Y-crown 316.

For the scaffold 300 there are 6 crests or peaks 311a and 6 troughs or valleys 311b for each ring 312. A crest 311a is always followed by a valley 311b. Ring 312b has 12 crowns: 3 are W-crowns 309, 3 are Y-crowns 310 and 6 are U-crowns 307.

A crimped diameter enforced on scaffold 300 (using, e.g., Process I or Process II) may be expressed in terms of a theoretical minimum crimped diameter where struts that converge at the same crown are in contact with each other when the scaffold is fully crimped, i.e., when the scaffold is removed from the crimping device, or when placed within a restraining sheath soon after crimping. The equation for the theoretical minimum crimped diameter (D-min) under these conditions is shown below $$D\text{-min} = (1/\pi) \times [(n \times \text{strut\_width}) + (m \times \text{link\_width})] + 2 \ast t$$

Where

"n" is the number of struts in a ring (12 struts for scaffold 300),

"strut_width" is the width of a strut (170 microns for scaffold 300),

"m" is the number of links adjoining adjacent rings (3 for scaffold 300),

"link_width" is the width of a link (127 microns for scaffold 300), and

"t" is the wall thickness (93 microns for scaffold 300).

Hence, for scaffold 300 in FIG. 5 D-min=(1/π)×[(12×170)+(3×127)]+2×(93)=957 microns.

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in claims should not be construed to limit the invention to the specific embodiments disclosed in the specification.

What is claimed is:

1. A method, comprising:
   using a scaffold made from a tube comprising a polymer, the polymer having a glass transition temperature, the scaffold having an outer diameter and the outer diameter having a before crimping size;
   using a crimping device having a plurality of blades configured to form an aperture, wherein the blades are rotated relative to each other to increase or decrease the size of the aperture during crimping;
   using a polymer material disposed within the aperture; and
   crimping the scaffold to a balloon, the crimping comprising:
      placing the scaffold and the balloon within the aperture, wherein the polymer material is between a surface of the scaffold and a surface of the blades,
      reducing the outer diameter of the scaffold from the before crimping size to a first size while the balloon has a first pressure,
      while the scaffold has about the first size and the balloon has a second pressure, resetting the polymer material,
      reducing the outer diameter of the scaffold from the about the first size to a second size while the balloon has the first pressure, and
      while the scaffold has about the second size and the balloon has the second pressure, resetting the polymer material.

2. The method of claim 1, wherein the second pressure is between about 1 atm to 4 atm or about 50% of a nominal balloon pressure.

3. The method of claim 1, wherein the scaffold is a thin-walled scaffold and the first pressure is about a rated burst pressure for the balloon, or about 200-300 psi.

4. The method of claim 1, wherein the crimping device is a film-headed crimper.

5. The method of claim 1, wherein the polymer material is polymer sheets.

6. The method of claim 1, wherein the polymer material comprises a sheath.

7. The method of claim 1, wherein the scaffold has a crimping temperature during crimping.

8. The method of claim 1, wherein the balloon has a nominal diameter, and wherein the before crimping size is greater than the nominal diameter.

9. The method of claim 1, the crimping step further including the step of removing the scaffold and balloon from the crimping device after the scaffold diameter is reduced to the first size, then returning the scaffold to the crimping device.

10. The method of claim 9, wherein the resetting of the polymer material while the scaffold has about the first size occurs when the scaffold and balloon are removed from the crimping device.

11. The method of claim 9, wherein the balloon is a first balloon, further including the step of replacing the first balloon with a second balloon of a balloon catheter when the scaffold is removed from the crimping device, and the scaffold is crimped to the second balloon.

12. The method of claim 9, wherein the scaffold diameter is reduced from the before crimping diameter to the first size using a first crimping device, and the scaffold diameter is reduced from the first size to the second size using a second crimping device.

13. The method of claim 1, wherein the polymer material within the aperture is re-set more than 2 times during the crimping.

14. The method of claim 1, wherein before and after reducing the scaffold diameter from the first size to the second size the aperture is held constant for a dwell period of between 1 seconds and 25 seconds.

15. A method, comprising:
using a scaffold made from a tube comprising a polymer, the polymer having a glass transition temperature, the scaffold having an outer diameter and the outer diameter having a before crimping size;
using a balloon having a nominal diameter;
using a polymer material disposable within an aperture of a crimping device; and
using the crimping device having a plurality of blades configured to form the aperture, wherein the blades are rotated relative to each other to increase or decrease a size of the aperture during crimping; and
crimping the scaffold to the balloon, the crimping comprising:
placing the scaffold and balloon within the aperture,
while the balloon has a first pressure, reducing the outer diameter of the scaffold from the before crimping size to a first size that is between 30% to 35% less than the before crimping size, after reducing the outer diameter to the first size and while the balloon has a second pressure, increasing the aperture size to remove a pressure of the blades from a surface of the scaffold, followed by removing excess polymer material from the aperture.

16. A method, comprising:
using a scaffold made from a tube comprising a polymer, the polymer having a glass transition temperature, the scaffold having an outer diameter and the outer diameter having a before crimping size;
using a balloon having a nominal diameter;
using a crimping device having a plurality of blades configured to form an aperture;
using a polymer material disposable within the aperture; and
crimping the scaffold to the balloon, the crimping comprising:
placing the scaffold and the balloon within the aperture so that the polymer material is between a scaffold surface and a surface of the blades,
reducing the outer diameter of the scaffold from the before crimping size to a second size, wherein the polymer material within the aperture is reset between 2 and 5 times while the scaffold outer diameter is reduced from the before crimping size to the second size; and
wherein the balloon has a first pressure when the scaffold outer diameter is reduced in size and a second pressure when the polymer material is reset.

17. The method of claim 16, wherein the polymer material comprises sheaths having different sizes.

18. The method of claim 16, wherein the polymer material are sheets operated by a film-headed crimper.

19. The method of claim 16, wherein the scaffold comprises struts forming rings, wherein neighboring rings are connected to each other by at least two links, and the scaffold is crimped to a theoretical minimum crimp size (D-min):

$$D\text{-min} = (1/\pi) \times [(n \times \text{strut\_width}) + (m \times \text{link\_width})] + 2*t$$

Where
"n" is the number of struts in a ring,
"strut_width" is the width of a strut,
"m" is the number of links adjoining adjacent rings,
"link_width" is the width of a link, and
"t" is the wall thickness.

* * * * *